(12) United States Patent
Yamakawa et al.

(10) Patent No.: US 6,699,880 B1
(45) Date of Patent: Mar. 2, 2004

(54) SUBSTITUTED IMIDAZOLIDINONE DERIVATIVES

(75) Inventors: Takeru Yamakawa, Tsukuba (JP); Makoto Ando, Tsukuba (JP); Seita Koito, Tokyo (JP); Kenji Ohwaki, Tsukuba (JP); Toshifumi Kimura, Tsukuba (JP); Toshihiko Saeki, Tsukuba (JP); Mitsuru Miyaji, Tsukuba (JP); Yuki Iwahori, Tsukuba (JP); Toru Fujikawa, Tsukuba (JP); Norikazu Otake, Tsukuba (JP); Kazuhito Noguchi, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/110,638

(22) PCT Filed: Oct. 13, 2000

(86) PCT No.: PCT/JP00/07133

§ 371 (c)(1),
(2), (4) Date: Apr. 15, 2002

(87) PCT Pub. No.: WO01/27104

PCT Pub. Date: Apr. 19, 2001

(30) Foreign Application Priority Data

Oct. 13, 1999 (JP) .................................. 11/291232

(51) Int. Cl.$^7$ ..................... A61K 31/445; C07D 401/14
(52) U.S. Cl. ........................................ 514/316; 546/187
(58) Field of Search ........................... 514/316; 546/187

(56) References Cited

U.S. PATENT DOCUMENTS

| | | | | | |
|---|---|---|---|---|---|
| 5,756,508 A | * | 5/1998 | Thompson et al. | ......... | 514/256 |
| 6,169,097 B1 | * | 1/2001 | Janssens et al. | ............ | 514/316 |

FOREIGN PATENT DOCUMENTS

| | | |
|---|---|---|
| WO | 96/13262 | 5/1996 |
| WO | 96/25934 | 8/1996 |
| WO | 99/32481 | 7/1999 |
| WO | 99/36421 | 7/1999 |

OTHER PUBLICATIONS

Bundgaard "Design of prodrugs" Elsevier p. 27–43 (1986).*
Jerusalinsky et al., NeuroReport, vol. 9, 1407–1411 (1998).
Bymaster et al., Life Sciences, vol. 64, Nos. 6/7, 527–534 (1999).
D'Agostino et al., Journal of Pharmacology and Experimental Therapeutics, vol. 283, No. 2, 750–756 (1997).
Oktay et al., Journal of Autonomic Pharmacology, vol. 18, 195–204 (1998).

* cited by examiner

*Primary Examiner*—Ceila Chang
(74) *Attorney, Agent, or Firm*—Wenderoth, Lind & Ponack, L.L.P.

(57) ABSTRACT

This invention relates to the compounds represented by the general formula [I],

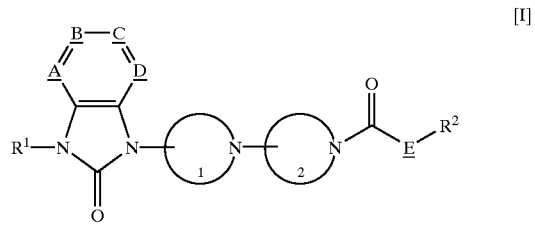

[in which A—D signify optionally substituted methine group(s) or nitrogen atom; E signifies oxygen or sulfur atom;

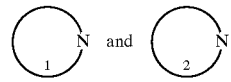

signify optionally substituted mono- or bi-cyclic aliphatic nitrogen-containing heterocyclic group(s); $R^1$ signifies lower alkenyl, lower alkynyl, cyclo(lower alkyl), lower alkanoyl, lower alkoxycarbonyl, optionally substituted lower alkyl and the like; and $R^2$ signifies lower alkyl].

The compounds of the present invention exhibit an action to stimulate muscarinic acetylcholine receptors M4, and are useful as analgesic for diseases accompanying pain such as cancerous pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis.

16 Claims, No Drawings

SUBSTITUTED IMIDAZOLIDINONE DERIVATIVES

This application is a 371 of PCT/JP00/07133 filed Oct. 13, 2000.

TECHNICAL FIELD

The present invention is useful in the medicinal field. More particularly, substituted imidazolidinone derivatives of the present invention have an action to stimulate muscarinic acetylcholine receptors M4, and are useful as analgesic for diseases accompanying pain such as cancerous pain, postoperative pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis.

BACKGROUND ART

Muscarinic agonists represented by acetylcholine are those which stimulate muscarinic acetylcholine receptors. Muscarinic agonists exhibit various pharmacological actions such as analgetic action, mnemonic action and: intraocular tension reducing action. Hence they are potential analgesic, agents for ameliorating symptoms of dementia, treating agents for glaucoma, or the like. However, conventional muscarinic agonists exhibit many side-effects and their clinical application is limited.

Recently, reports are made suggesting that such pharmacological actions of a muscarine agonist are expressed through M4 receptor subtype among muscarinic acetylcholine receptors. For example, it was reported that the analgesic action of muscarinic agonists was blocked by administration of m4 toxin which is an M4-selective antagonist, and also that intracerebral administration of m4 toxin alome caused memory defects [cf. *Neuroreport*, Vol.9, No.7, pp.1407–1411 (1998)]. It is also suggested, furthermore, that M4 receptors participate in various physiological activities such as amelioration of schizophrenia symptoms, contraction of the gallbladder or relaxation of smooth muscle of the bladder [cf. e.g. *Life Sciences*, Vol.64, June–July, pp527–534 (1999); *Journal of Pharmacology and Experimental Therapeutics*, Vol.283, No.2, pp.750–756 (1997); *Journal of Autonomic Pharmacology*, Vol.18, No.4, pp.195–204 (1998)].

Therefore, substances which selectively stimulate M4 receptors can be expected to have utilities as, for example, analgesic for diseases accompanying pain such as cancerous pain, postoperative pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis.

Compounds which are structurally analogous to the compounds of the present invention are disclosed in International Publications, e.g. WO96/13262 and WO99/32481. However, those prior art publications contain no specific disclosure or suggestion about the compounds of the, present invention. Neither do they teach anything at all about the M4 receptors-stimulating action.

DISCLOSURE OF THE INVENTION

The object of the present invention is to provide novel analgesic and agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis, which have M4 receptors-stimulating action.

We have discovered that compounds represented by a general formula [I]

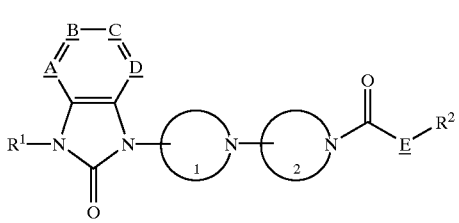

[I]

[in which $\underline{A}$, $\underline{B}$, $\underline{C}$ and $\underline{D}$ are same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl) aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy-carbonylamino, aminosulfonyl, lower alkylaminosulfonyl, di(lower alkyl) aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino; $\underline{E}$ signifies oxygen or sulfur;

are same or different and signify $C_3$–$C_9$ mono- or bi-cyclic aliphatic nitrogen-containing heterocyclic group(s) which may be substituted with halogen or lower alkyl; $R_1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl) carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl) amino, (lower alkylamino)sulfonylamino and (di-lower alkylamino)sulfonylamino; and $R^2$ signifies lower alkyl] possess high M4 receptors-stimulating action and are useful as analgesic for diseases accompanying pain such as cancerous pain, postoperative pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel, syndrome, schizophrenia, glaucoma, pollakiuria, urinary incontinence, cholelithiasis, cholecystitis, functional dyspepsia and reflux esophagitis, and completed the present invention.

The present invention relates to those compounds represented by Formula [I], salts thereof, their production processes and uses.

The symbols and the terms used in the present specification shall be explained.

"Halogen" means fluorine, chlorine, bromine and iodine atoms.

"Lower alkyl" means a $C_1$–$C_6$ linear or branched alkyl group, examples of which include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl 1,1,2-trimethylpropyl, 1,2,2-trimethylpropyl, 1-ethyl-2-methylpropyl and 1-ethyl-1-methylpropyl groups.

"Lower alkenyl" means a $C_2$–$C_6$ linear or branched alkenyl group, examples of which include vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl and 4-pentenyl groups.

"Lower alkynyl" means a $C_2$–$C_6$ linear or branched alkynyl group, examples of which include ethynyl, 2-propynyl, 1-methyl-2-propynyl, 2-butynyl, 1-methyl-2-butynyl, 2-pentynyl, 3-pentynyl and 4-pentynyl groups.

"Cyclo(lower alkyl)" means a $C_3$–$C_6$ cycloalkyl group, examples of which include cyclopropyl, cyclobutyl, cyclopentyl and cyclohexyl groups.

"Lower alkylamino" means an amino group which is mono-substituted with an above-named lower alkyl group, examples of which include methylamino, ethylamino, propylamino, isopropylamino, butylamino, sec-butylamino and tert-butylamino groups.

"Di(lower alkyl)amino" means an amino group which is di-substituted with above-named lower alkyl group(s), examples of which include dimethylamino, diethylamino, ethylmethylamino, dipropylamino, methylpropylamino and diisopropylamino groups.

"Lower alkythio" means an alkylthio group having an above-named lower alkyl group, examples of which include methylthio, ethylthio, propylthio, isopropylthio, butylthio, sec-butylthio and tert-butylthio groups.

"Lower alkylsulfinyl" means an alkylsulfinyl group having an aforesaid lower alkyl group, examples of which include methylsulfinyl, ethylsulfinyl, propylsulfinyl, isopropylsulfinyl, butylsulfinyl, sec-butylsulfinyl and tert-butylsulfinyl groups.

"Lower alkylsulfonyl" means an alkylsulfonyl group having an aforesaid lower alkyl group, examples of which include methylsulfonyl, ethylsulfonyl, propylsulfonyl, isopropylsulfonyl, butylsulfonyl, sec-butylsulfonyl and tert-butylsulfonyl.

"Lower alkoxy" means an alkoxy group having an aforesaid alkyl group, i.e., a $C_1$–$C_6$ alkoxy group, examples of which include methoxy, ethoxy, propoxy, isopropoxy, butoxy, isobutoxy, tert-butoxy and pentyloxy groups.

"Optionally fluorine-substituted lower alkoxy" means an aforesaid lower alkoxy group whose substitutable, optional position(s) may be substituted with one or two or more, preferably 1–3, fluorine atoms, examples of which include, in addition to the above-exemplified alkoxy groups, fluoromethoxy, difluoromethoxy, trifluoromethoxy, 1,2-difluoroethoxy and 2,2-difluoroethoxy groups.

"Lower alkanoyl" means an alkanoyl group having an aforesaid lower alkyl group, i.e., a $C_2$–$C_7$ alkanoyl group, examples of which include acetyl propionyl, butyryl, isobutyryl, valeryl, isovaleryl and pivaloyl groups.

"Lower alkoxycarbonyl" means an alkoxycarbonyl group having an aforesaid lower alkoxy group, i.e., a $C_2$–$C_7$ alkoxycarbonyl group, examples of which include methoxycarbonyl, ethoxycarbonyl, propoxycarbonyl, isopropoxycarbonyl, butoxycarbonyl, isobutoxycarbonyl, tert-butoxycarbonyl and pentyloxycarbonyl groups.

"Lower alkylcarbamoyl" means a carbamoyl group which is mono-substituted with an aforesaid lower alkyl group, examples of which include methylcabamoyl, ethylcarbamoyl, propylcarbamoyl, isopropylcarbamoyl, butylcarbamoyl, sec-butylcarbamoyl and tert-butylcarbamoyl groups.

"Di(lower alkyl)carbamoyl" means a carbamoyl group which is di-substituted with aforesaid lower alkyl group(s), examples of which include dimethylcarbamoyl, diethylcarbamoyl, ethylmethylcarbamoyl, dipropylcarbamoyl, methylpropylcarbamoyl and diisopropylcarbamoyl groups.

"Lower alkylaminosulfonyl" means an alkylaminosulfonyl group having an aforesaid lower alkylamino group, examples of which include methylaminosulfonyl, ethylaminosulfonyl, propylaminosulfonyl, isopropylaminosulfonyl, butylaminosulfonyl, sec-butylaminosulfonyl and tert-butylaminosulfonyl groups.

"Di(lower alkyl)aminosulfonyl" means a dialkylaminosulfonyl group having an aforesaid di-lower alkylamino group, examples of which include dimethylaminosulfonyl, diethylaminosulfonyl, ethylmethylaminosulfonyl, dipropylaminosulfonyl, methylpropylaminosulfonyl and diisopropylaminosulfonyl groups.

"Lower alkylcarbamoyloxy" means an alkylcarbamoyloxy group having an aforesaid lower alkylcarbamoyl group, examples of which include methylcarbamoyloxy, ethylcarbamoyloxy, propylcarbamoyloxy, isopropylcarbamoyloxy, butylcarbamoyloxy, sec-butylcarbamoyloxy and tert-butylcarbamoyloxy groups.

"Di(lower alkyl)carbamoyloxy" means a dialkylcarbamoyloxy group having an aforesaid di-lower alkylcarbamoyl group, examples of which include dimethylcarbamoyloxy, diethylcarbamoyloxy, ethylmethylcarbamoyloxy, dipropylcarbamoyloxy, methylpropylcarbamoyloxy and diisopropylcarbamoyloxy groups.

"Lower alkoxycarbonylamino" means an amino group which is mono-substituted with an aforesaid lower alkoxycarbonyl group, examples of which include methoxycarbonylamino, ethoxycarbonylamino, propoxycarbonylamino, isopropoxycarbonylamino, butoxycarbonylaino, isobutoxycarbonylamino, tert-butoxycarbonylamino and pentyloxycarbonylamino groups.

"(Lower alkylamino)sulfonylamino" means an amino group which is mono-substituted with an aforesaid lower alkylaminosulfonyl group, examples of which include (methylamino)sulfonylamino, (ethylamino)sulfonylamino, (propylamino)sulfonylamino, (isopropylamino)sulfonylamino, (butylamino)sulfonylamino, (sec-butylamino) sulfonylamino and (tert-butylamino)sulfonylamino groups.

"(Di-lower alkylamino)sulfonylamino" means an amino group which is mono-substituted with an aforesaid di-lower alkylaminosulfonyl group, examples of which include (dimethylamino)sulfonylamino, (diethylamino) sulfonylamino, (ethylmethylamino)sulfonylamino, (dipropylamino)sulfonylamino, (methylpropylamino) sulfonylamino and (diisopropylamino)sulfonylamino groups.

"(Lower alkylaminosulfonyl)(lower alkyl)amino" means an amino group which is substituted with an aforesaid lower alkylaminosulfonyl group and an aforesaid lower alkyl group, examples of which include methyl(methylaminosulfonyl)amino, (ethylamino-sulfonyl)methylamino groups.

"(Di-lower alkylaminosulfonyl)(lower alkyl)amino" means an amino group which is substituted with an aforesaid di-lower alkylaminosulfonyl group and an aforesaid lower alkyl group, examples of which include (dimethylaminosulfonyl)methylamino and (diethylaminosulfonyl) methylamino groups.

"Mono- or bi-cyclic aliphatic nitrogen-containing heterocyclic group" means a mono- or bi-cyclic group which is a saturated aliphatic heterocyclic group containing at least one nitrogen atom as a ring-forming member, examples of which include those groups expressed by the following formulae:

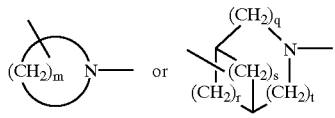

(in which m signifies an integer of 3–7; q, r and t, which may be same or different, each signifies an integer of 0–3; s signifies an integer of 1–4; and the sum of q, r, s and t not exceeding 7).

"Lower alkylsulfonylamino" means an amino group which is mono-substituted with an aforesaid lower alkylsulfonyl group, examples of which include methylsulfonylamino, ethylsulfonylamino, propylsulfonylamino, isopropylsulfonylamino, butylsulfonylamino, sec-butylsulfonylamino and tert-butylsulfonylamino groups.

"(Lower alkylcarbamoyl)amino" means an amino group which is mono-substituted with an aforesaid lower alkylcarbamoyl group, examples of which include (methylcarbamoyl)amino, (ethylcarbamoyl)amino, (propylcarbamoyl)amino, (isopropylcarbamoyl)amino, (butylcarbamoyl) amino, (sec-butylcarbamoyl)amino and (tert-butylcarbamoyl)amino groups.

"(Di-lower alkylcarbamoyl)amino" means an amino group which is mono-substituted with an aforesaid di-lower alkylcarbamoyl group, examples of which include (dimethylcarbamoyl)amino, (diethylcarbamoyl)amino, (ethylmethylcarbamoyl)amino, (dipropylcarbamoyl)amino, (methylpropylcarbamoyl)amino and (diisopropylcarbamoyl)amino groups.

"Salts" of those compounds which are represented by the general formula [I] means customary, pharmaceutically acceptable ones, for examples, acid addition salts at the basic heterocyclic groups. As such acid addition salts, for example, inorganic acid salts, e.g., hydrochloride, hydrobromide, sulfate, nitrate, phosphate, perchlorate and the like; organic acid salts such as maleate, fumarate, tartarate, citrate, ascorbate, benzoate, trifluoroacetate and the like; and sulfonic acid salts such as methanesulfonate, isethionate, benzenesulfonate, p-toluenesulfonate and the like may be named.

"Treating agent" means drugs which are used for treatment and/or prophylaxis of various diseases.

For disclosing the compounds of the present invention, which are represented by the general formula [I], more specifically, those marks or symbols used in said formula [I] are explained in further details, referring to preferred specific examples.

Those compounds of the general formula [I] of the present invention in occasions may have stereoisomers such as optical isomers, diastereomers, geometrical isomers and the like, depending on the conditions of their substituents. The compounds of the general formula [I] of the present invention cover all of these stereoisomers and their mixtures.

To avoid any unnecessary confusion, position numbers of the 2-oxoimidazole ring moiety of the compounds of the present invention are set as in the following formula [a] throughout in the specification, for nominating individual compounds and providing other explanations.

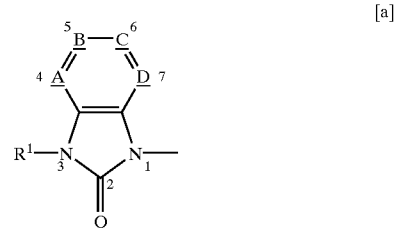

A, B, C and D are same or different and signify methine group(s) or nitrogen atom, said methine group(s) being optionally substituted with cyano, halogen, hydroxyl, cyclo (lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl) aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino.

As the substituent halogen atom, for example, fluorine, chlorine and bromine atoms are preferred.

As the substituent cyclo(lower alkyl), for example, cyclopropyl and cyclobutyl groups are preferred.

As the substituent lower alkylthio, for example, methylthio, ethylthio and propylthio groups are preferred.

As the substituent lower alkylsulfinyl, for example, methylsulfinyl and ethylsulfinyl groups are preferred.

As the substituent lower alkylsulfonyl, for example, methylsulfonyl, ethylsulfonyl and propylsulfonyl groups are preferred.

As the substituent optionally fluorine-substituted lower alkoxy, for example, methoxy, ethoxy, propoxy, fluoromethoxy and 2,2-difluoroethoxy groups are preferred.

As the substituent lower alkanoyl, for example, acetyl, propionyl and butyryl groups are preferred.

As the substituent lower alkoxycarbonyl, for example, methoxycarbonyl, ethoxycarbonyl and propoxycarbonyl groups are preferred.

As the substituent lower alkylcarbamoyl, for example, methylcarbamoyl, ethylcarbamoyl and propylcarbamoyl groups are preferred.

As the substituent di(lower alkyl)carbamoyl, for example, dimethylcarbamoyl, diethylcarbamoyl and dipropylcarbamoyl groups are preferred.

As the substituent lower alkylaminosulfonyl, for example, methylaminosulfonyl and ethylaminosulfonyl groups are preferred.

As the substituent di(lower alkyl)aminosulfonyl, for example, dimethylaminosulfonyl and diethylaminosulfonyl groups are preferred.

The substituent "lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxycarbonylamino, aminosulfonyl, lower alkylaminosulfonyl, di(lower alkyl) aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino" means named lower alkyl groups which are unsubstituted and those named lower alkyl groups which are substituted at substitutable, optional position(s). One, two or more, preferably one or two, same or different substituents can be selected from the group consisting of halogen, hydroxyl, amino, lower alkylamino, di(lower alkyl) amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl)aminosulfonyl, (lower alkylamino)sulfonylamino, (di-lower alkylamino) sulfonylamino, (lower alkylaminosulfonyl)(lower alkyl) amino and (di-lower alkylaminosulfonyl)(lower alkyl) amino.

As the substituent halogen, for example, fluorine atom is preferred.

As the substituent lower alkylamino, for example, methylamino and ethylamino groups are preferred.

As the substituent di(lower alkyl)amino, for example, dimethylamino and diethylamino groups are preferred.

As the substituent lower alkylthio, for example, methylthio and ethylthio groups are preferred.

As the substituent lower alkylsulfinyl, for example, methylsulfinyl and ethylsulfinyl groups are preferred.

As the substituent lower alkylsulfonyl, for example, methylsulfonyl, ethylsulfonyl and propylsulfonyl groups are preferred.

As the substituent optionally fluorine-substituted lower alkoxy, for example, methoxy, ethoxy, propoxy, fluoromethoxy and 2,2-difluoroethoxy groups are preferred.

As the substituent lower alkanoyl, for example, acetyl and propionyl groups are preferred.

As the substituent lower alkoxycarbonyl, for example, methoxycarbonyl and ethoxycarbonyl groups are preferred.

As the substituent lower alkylcarbamoyl, for example, methylcarbamoyl and ethylcarbamoyl groups are preferred.

As the substituent di(lower alkyl)carbamoyl, for example, dimethylcarbamoyl group is preferred.

As the substituent lower alkylcarbamoyloxy, for example, methylcarbamoyloxy group is preferred.

As the substituent di(lower alkyl)carbamoyloxy, for example, dimethylcarbamoyloxy group is preferred.

As the substituent lower alkoxycarbonylamino, for example, methoxycarbonylamino and ethoxycarbonylamino groups are preferred.

As the substituent lower alkylaminosulfonyl, for example, methylaminosulfonyl and ethylaminosulfonyl groups are preferred.

As the substituent di(lower alkyl)aminosulfonyl, for example, dimethylaminosulfonyl and diethylaminosulfonyl groups are preferred.

As the substituent (lower alkylamino)sulfonylamino, for example, (methylamino)sulfonylamino and (ethylamino) sulfonylamino groups are preferred.

As the substituent (di-lower alkylamino)sulfonylamino, for example, (dimethylamino)sulfonylamino and (diethylamino)sulfonylamino groups are preferred.

As the substituent (lower alkylaminosulfonyl)(lower alkyl)amino, for example, methyl(methylaminosulfonyl) amino group is preferred.

As the substituent (di-lower alkylaminosulfonyl)(lower alkyl)amino, for example, (dimethylaminosulfonyl) methylamino group is preferred.

As the substituents on said lower alkyl group, for example, halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, lower alkylcarbamoyloxy, di(lower alkyl)carbamoyloxy, lower alkoxycarbonylamino, aminosulfonyl, lower alkylaminosulfonyl, di(lower alkyl)aminosulfonyl, (lower alkylamino)sulfonylamino, (di-lower alkylamino) sulfonylamino groups are preferred. In particular, lower alkylsulfonyl and lower alkoxycarbonylamino groups are preferred.

As the "lower alkyl" itself which may have above substituent(s), for example, methyl, ethyl, propyl, in particular, methyl, are preferred.

Therefore, preferred examples of those optionally substituted lower alkyl groups include, methyl, ethyl, fluoromethyl, 2-fluoroethyl, 2,2-difluoroethyl, 2-hydroxyethyl, 2-aminoethyl, 2-methylaminoethyl, dimethylaminomethyl, 2-(dimethylamino)ethyl, methylthiomethyl, methylsulfinylmethyl, methylsulfonylmethyl, ethylsulfonylmethyl, propylsulfonylmethyl, 2-methylsulfonylethyl, 2-ethylsulfonylethyl, methoxymethyl, ethoxymethyl, propoxymethyl, 2-methoxyethyl, 2-ethoxyethyl, acetylmethyl, propionylmethyl, 2-acetylethyl, methoxycarbonylmethyl, ethoxycarbonylmethyl, 2-methoxycarbonylethyl, 2-ethoxycarbonylethyl, carbamoylmethyl, 2-carbamoylethyl, methylcarbamoylmethyl, ethylcarbamoylmethyl, 2-(methylcarbamoyl)ethyl, dimethylcarbamoylmethyl, 2-(dimethylcarbamoyl)ethyl, methylcarbamoyloxymethyl, 2-(methylcarbamoyloxy)ethyl, dimethylcarbamoyloxymethyl, (methoxycarbonylamino)methyl, (ethoxycarbonylamino)methyl, 2-(methoxycarbonylamino) ethyl, 2-(ethoxycarbonylamino)ethyl, aminosulfonylmethyl, methylaminosulfonylmethyl, dimethylaminosulfonylmethyl, 2-(dimethylaminosulfonyl)ethyl, [(methylaminosulfonyl)amino]methyl and [(dimethylaminosulfonyl) amino]methyl. Of those, methyl, methylsulfonylmethyl, ethylsulfonylmethyl and (methoxycarbonylamino)methyl groups are particularly preferred.

As the substituents on the methine group, for example, halogen, hydroxyl, lower alkylsulfonyl, optionally fluorine-substituted lower alkoxy, di(lower alkyl)carbamoyl, di(lower alkyl)aminosulfonyl and those optionally substituted lower alkyl groups are preferred.

In particular, halogen, hydroxyl, lower alkylsulfonyl, and above-named optionally substituted lower alkyl groups are preferred.

As A, B, C and D, same or different methine groups which may have above-named substituent groups are preferred.

Accordingly, as the groups represented by the formula

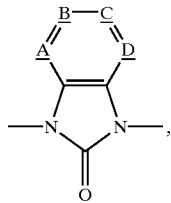

preferred are those formed from, for example,
1,3-dihydro-2H-benzimidazol-2-one,
4-fluoro-1,3-dihydro-2H-benzimidazol-2-one,
5-fluoro-1,3-dihydro-2H-benzimidazol-2-one,
6-fluoro-1,3-dihydro-2H-benzimidazol-2-one,
7-fluoro-1,3-dihydro-2H-benzimidazol-2-one,
4-chloro-1,3-dihydro-2H-benzimidazol-2-one,
5-chloro-1,3-dihydro-2H-benzimidazol-2-one,
6-chloro-1,3-dihydro-2H-benzimidazol-2-one,
7-chloro-1,3-dihydro-2H-benzimidazol-2-one,
5-bromo-1,3-dihydro-2H-benzimidazol-2-one,
4-hydroxy-1,3-dihydro-2H-benzimidazol-2-one,
5-hydroxy-1,3-dihydro-2H-benzimidazol-2-one,
6-hydroxy-1,3-dihydro-2H-benzimidazol-2-one,
7-hydroxy-1,3-dihydro-2H-benzimidazol-2-one,
4-methyl-1,3-dihydro-2H-benzimidazol-2-one,
5-methyl-1,3-dihydro-2H-benzimidazol-2-one,
6-methyl-1,3-dihydro-2H-benzimidazol-2-one,
7-methyl-1,3-dihydro-2H-benzimidazol-2-one,
4-ethyl-1,3-dihydro-2H-benzimidazol-2-one,
5-ethyl-1,3-dihydro-2H-benzimidazol-2-one,
6-ethyl-1,3-dihydro-2H-benzimidazol-2-one,
7-ethyl-1,3-dihydro-2H-benzimidazol-2-one,
4-propyl-1,3-dihydro-2H-benzimidazol-2-one,
5-propyl-1,3-dihydro-2H-benzimidazol-2-one,
6-propyl-1,3-dihydro-2H-benzimidazol-2-one,
7-propyl-1,3-dihydro-2H-benzimidazol-2-one,
4-methylthio-1,3-dihydro-2H-benzimidazol-2-one,
5-methylthio-1,3-dihydro-2H-benzimidazol-2-one,
6-methylthio-1,3-dihydro-2H-benzimidazol-2-one,
7-methylthio-1,3-dihydro-2H-benzimidazol-2-one,
4-ethylthio-1,3-dihydro-2H-benzimidazol-2-one,
5-ethylthio-1,3-dihydro-2H-benzimidazol-2-one,
4-propylthio-1,3-dihydro-2H-benzimidazol-2-one,
5-propylthio-1,3-dihydro-2H-benzimidazol-2-one,
4-methylsulfinyl-1,3-dihydro-2H-benzimidazol-2-one,
5-methylsulfinyl-1,3-dihydro-2H-benzimidazol-2-one,
4-methylsulfonyl-1,3-dihydro-2H-benzimidazol-2-one,
5-methylsulfonyl-1,3-dihydro-2H-benzimidazol-2-one,
6-methylsulfonyl-1,3-dihydro-2H-benzimidazol-2-one,
7-methylsulfonyl-1,3-dihydro-2H-benzimidazol-2-one,
4-ethylsulfonyl-1,3-dihydro-2H-benzimidazol-2-one,
5-ethylsulfonyl-1,3-dihydro-2H-benzimidazol-2-one,
6-ethylsulfonyl-1,3-dihydro-2H-benzimidazol-2-one,
7-ethylsulfonyl-1,3-dihydro-2H-benzimidazol-2-one,
4-propylsulfonyl-1,3-dihydro-2H-benzimidazol-2-one,
5-propylsulfonyl-1,3-dihydro-2H-benzimidazol-2-one,
6-propylsulfonyl-1,3-dihydro-2H-benzimidazol-2-one,
4-methoxy-1,3-dihydro-2H-benzimidazol-2-one,
5-methoxy-1,3-dihydro-2H-benzimidazol-2-one,
6-methoxy-1,3-dihydro-2H-benzimidazol-2-one,
7-methoxy-1,3-dihydro-2H-benzimidazol-2-one,
4-ethoxy-1,3-dihydro-2H-benzimidazol-2-one,
5-ethoxy-1,3-dihydro-2H-benzimidazol-2-one,
6-ethoxy-1,3-dihydro-2H-benzimidazol-2-one,
7-ethoxy-1,3-dihydro-2H-benzimidazol-2-one,
4-propoxy-1,3-dihydro-2H-benzimidazol-2-one,
5-propoxy-1,3-dihydro-2H-benzimidazol-2-one,
4-acetyl-1,3-dihydro-2H-benzimidazol-2-one,
5-acetyl-1,3-dihydro-2H-benzimidazol-2-one,
6-acetyl-1,3-dihydro-2H-benzimidazol-2-one,
4-propionyl-1,3-dihydro-2H-benzimidazol-2-one,
5-propionyl-1,3-dihydro-2H-benzimidazol-2-one,
4-butyryl-1,3-dihydro-2H-benzimidazol-2-one,
5-butyryl-1,3-dihydro-2H-benzimidazol-2-one,
4-methoxycarbonyl-1,3-dihydro-2H-benzimidazol-2-one,
5-methoxycarbonyl-1,3-dihydro-2H-benzimidazol-2-one,
6-methoxycarbonyl-1,3-dihydro-2H-benzimidazol-2-one,
4-ethoxycarbonyl-1,3-dihydro-2H-benzimidazol-2-one,
5-ethoxycarbonyl-1,3-dihydro-2H-benzimidazol-2-one,
4-propoxycarbonyl-1,3-dihydro-2H-benzimidazol-2-one,
5-propoxycarbonyl-1,3-dihydro-2H-benzimidazol-2-one,
4-carbamoyl-1,3-dihydro-2H-benzimidazol-2-one,
5-carbamoyl-1,3-dihydro-2H-benzimidazol-2-one,
6-carbamoyl-1,3-dihydro-2H-benzimidazol-2-one,
4-methylcarbamoyl-1,3-dihydro-2H-benzimidazol-2-one,
5-methylcarbamoyl-1,3-dihydro-2H-benzimidazol-2-one,
4-ethylcarbamoyl-1,3-dihydro-2H-benzimidazol-2-one,
5-ethylcarbamoyl-1,3-dihydro-2H-benzimidazol-2-one,
4-propylcarbamoyl-1,3-dihydro-2H-benzimidazol-2-one,
5-propylcarbamoyl-1,3-dihydro-2H-benzimidazol-2-one,
4-dimethylcarbamoyl-1,3-dihydro-2H-benzimidazol-2-one,
5-dimethylcarbamoyl-1,3-dihydro-2H-benzimidazol-2-one,
4-diethylcarbamoyl-1,3-dihydro-2H-benzimidazol-2-one,
5-diethylcarbamoyl-1,3-dihydro-2H-benzimidazol-2-one,
4-dipropylcarbamoyl-1,3-dihydro-2H-benzimidazol-2-one,
5-dipropylcarbamoyl-1,3-dihydro-2H-benzimidazol-2-one,
4-aminosulfonyl-1,3-dihydro-2H-benzimidazol-2-one,
5-aminosulfonyl-1,3-dihydro-2H-benzimidazol-2-one,
4-methylaminosulfonyl-1,3-dihydro-2H-benzimidazol-2-one,
5-methylaminosulfonyl-1,3-dihydro-2H-benzimidazol-2-one,
4-dimethylaminosulfonyl-1,3-dihydro-2H-benzimidazol-2-one,
5-dimethylaminosulfonyl-1,3-dihydro-2H-benzimidazol-2-one,
4-fluoromethyl-1,3-dihydro-2H-benzimidazol-2-one,
4-fluoromethyl-1,3-dihydro-2H-benzimidazol-2-one,
4-(2-fluoroethyl)-1,3-dihydro-2H-benzimidazol-2-one,
5-(2-fluoroethyl)-1,3-dihydro-2H-benzimidazol-2-one,
4-(2,2-difluoroethyl)-1,3-dihydro-2H-benzimidazol-2-one,
5-(2,2-difluoroethyl)-1,3-dihydro-2H-benzimidazol-2-one,
4-(2-hydroxyethyl)-1,3-dihydro-2H-benzimidazol-2-one,
5-(2-hydroxyethyl)-1,3-dihydro-2H-benzimidazol-2-one,
4-aminomethyl-1,3-dihydro-2H-benzimidazol-2-one,
5-aminomethyl-1,3-dihydro-2H-benzimidazol-2-one,
4-methylaminomethyl-1,3-dihydro-2H-benzimidazol-2-one,
5-methylaminomethyl-1,3-dihydro-2H-benzimidazol-2-one,
4-dimethylaminomethyl-1,3-dihydro-2H benzimidazol-2-one,
5-dimethylaminomethyl-1,3-dihydro-2H-benzimidazol-2-one,
4-methylthiomethyl-1,3-dihydro-2H-benzimidazol-2-one,
5-methylthiomethyl-1,3-dihydro-2H-benzimidazol-2-one,
4-methylsulfinylmethyl-1,3-dihydro-2H-benzimidazol-2-one,
5-methylsulfinylmethyl-1,3-dihydro-2H-benzimidazol-2-one, 4-methylsulfonylmethyl-1,3-dihydro-2H-benzimidazol-2-one,
5-methylsulfonylmethyl-1,3-dihydro-2H-benzimidazol-2-one,
4-ethylsulfonylmethyl-1,3-dihydro-2H-benzimidazol-2-one,
5-ethylsulfonylmethyl-1,3-dihydro-2H-benzimidazol-2-one,
4-propylsulfonylmethyl-1,3-dihydro-2H-benzimidazol-2-one,
5-propylsulfonylmethyl-1,3-dihydro-2H-benzimidazol-2-one,
4-(2-methylsulfonylethyl)-1,3-dihydro-2H-benzimidazol-2-one,
5-(2-methylsulfonylethyl)-1,3-dihydro-2H-benzimidazol-2-one,
4-(2-ethylsulfonylethyl)-1,3-dihydro-2H-benzimidazol-2-one,
5-(2-ethylsulfonylethyl)-1,3-dihydro-2H-benzimidazol-2-one,
4-methoxymethyl-1,3-dihydro-2H-benzimidazol-2-one,
5-methoxymethyl-1,3-dihydro-2H-benzimidazol-2-one,
4-ethoxymethyl-1,3-dihydro-2H-benzimidazol-2-one,
5-ethoxymethyl-1,3-dihydro-2H-benzimidazol-2-one,
4-propoxymethyl-1,3-dihydro-2H-benzimidazol-2-one,
5-propoxymethyl-1,3-dihydro-2H-benzimidazol-2-one,
4-(2-methoxyethyl)-1,3-dihydro-2H-benzimidazol-2-one,
5-(2-methoxyethyl)-1,3-dihydro-2H-benzimidazol-2-one,
4-(2-ethoxyethyl)-1,3-dihydro-2H-benzimidazol-2-one,
5-(2-ethoxyethyl)-1,3-dihydro-2H-benzimidazol-2-one,
4-acetylmethyl-1,3-dihydro-2H-benzimidazol-2-one,
5-acetylmethyl-1,3-dihydro-2H-benzimidazol-2-one,
4-propionylmethyl-1,3-dihydro-2H-benzimidazol-2-one,
5-propionylmethyl-1,3-dihydro-2H-benzimidazol-2-one,
4-(2-acetylethyl)-1,3-dihydro-2H-benzimidazol-2-one,
5-(2-acetylethyl)-1,3-dihydro-2H-benzimidazol-2-one,
4-methoxycarbonylmethyl-1,3-dihydro-2H-benzimidazol-2-one,
5-methoxycarbonylmethyl-1,3-dihydro-2H-benzimidazol-2-one,
4-ethoxycarbonylmethyl-1,3-dihydro-2H-benzimidazol-2-one,
5-ethoxycarbonylmethyl-1,3-dihydro-2H-benzimidazol-2-one,
4-(2-methoxycarbonylethyl)-1,3-dihydro-2H-benzimidazol-2-one,
5-(2-methoxycarbonylethyl)-1,3-dihydro-2H-benzimidazol-2-one,
4-(2-ethoxycarbonylethyl)-1,3-dihydro-2H-benzimidazol-2-one,
5-(2-ethoxycarbonylethyl)-1,3-dihydro-2H-benzimidazol-2-one,
4-(methoxycarbonylamino)methyl-1,3-dihydro-2H-benzimidazol-2-one
5-(methoxycarbonylamino)methyl-1,3-dihydro-2H-benzimidazol-2-one
4-(ethoxycarbonylamino)methyl-1,3-dihydro-2H-benzimidazol-2-one,
5-(ethoxycarbonylamino)methyl-1,3-dihydro-2H-benzimidazol-2-one,
4-[2-(methoxycarbonylamino)ethyl]-1,3-dihydro-2H-benzimidazol-2-one,
5-[2-(methoxycarbonylamino)ethyl]-1,3-dihydro-2H-benzimidazol-2-one,
4-[2-(ethoxycarbonylamino)ethyl]-1,3-dihydro-2H-benzimidazol-2-one,
4-[2-(ethoxycarbonylamino)ethyl]-1,3-dihydro-2H-benzimidazol-2-one,
4-carbamoylmethyl-1,3-dihydro-2H-benzimidazol-2-one,
5-carbamoylmethyl-1,3-dihydro-2H-benzimidazol-2-one,
4-(2-carbamoylethyl)-1,3-dihydro-2H-benzimidazol-2-one,
5-(2-carbamoylethyl)-1,3-dihydro-2H-benzimidazol-2-one,
4-methylcarbamoylmethyl-1,3-dihydro-2H-benzimidazol-2-one,
5-methylcarbamoylmethyl-1,3-dihydro-2H-benzimidazol-2-one,
4-ethylcarbamoylmethyl-1,3-dihydro-2H-benzimidazol-2-one,
5-ethylcarbamoylmethyl-1,3-dihydro-2H-benzimidazol-2-one,
4-[2-(methylcarbamoyl)ethyl]-1,3-dihydro-2H-benzimidazol-2-one,
5-[2-(methylcarbamoyl)ethyl]-1,3-dihydro-2H-benzimidazol-2-one,
4-dimethylcarbamoylmethyl-1,3-dihydro-2H-benzimidazol-2-one,
5-dimethylcarbamoylmethyl-1,3-dihydro-2H-benzimidazol-2-one,
4-[2-(dimethylcarbamoyl)ethyl]-1,3-dihydro-2H-benzimidazol-2-one,
5-[2-(dimethylearbamoyl)ethyl]-1,3-dihydro-2H-benzimidazol-2-one,
4-methylcarbamoyloxymethyl-1,3-dihydro-2H-benzimidazol-2-one,
5-methylcarbamoyloxymethyl-1,3-dihydro-2H-benzimidazol-2-one,
4-[2-(methylcarbamoyloxy)ethyl]-1,3-dihydro-2H-benzimidazol-2-one,
5-[2-(methylcarbamoyloxy)ethyl]-1,3-dihydro-2H-benzimidazol-2-one,
4-dimethylcarbamoyloxymethyl-1,3-dihydro-2H-benzimidazol-2-one,
5-dimethylcarbamoyloxymethyl-1,3-dihydro-2H-benzimidazol-2-one,
4-aminosulfonylmethyl-1,3-dihydro-2H-benzimidazol-2-one,
5-aminosulfonylmethyl-1,3-dihydro-2H-benzimidazol-2-one,
4-methylaminosulfonylmethyl-1,3-dihydro-2H-benzimidazol-2-one,
5-methylaminosulfonylmethyl-1,3-dihydro-2H-benzimidazol-2-one,
4-dimethylaminosulfonylmethyl-1,3-dihydro-2H-benzimidazol-2-one,
5-dimethylaminosulfonylmethyl-1,3-dihydro-2H-benzimidazol-2-one,
4-[2-(dimethylaminosulfonyl)ethyl]-1,3-dihydro-2H-benzimidazol-2-one,
5-[2-(dimethylaminosulfonyl)ethyl]-1,3-dihydro-2H-benzimidazol-2-one,
4-[(methylaminosulfonyl)amino]methyl-1,3-dihydro-2H-benzimidazol-2-one,
5-[(methylaminosulfonyl)amino]methyl-1,3-dihydro-2H-benzimidazol-2-one,
4-[(dimethylaminosulfonyl)amino]methyl-1,3-dihydro-2H-benzimidazol-2-one, and
5-[(dimethylaminosulfonyl)amino]methyl-1,3-dihydro-2H-benzimidazol-2-one,
Of those, groups formed of 1,3-dihydro-2H-benzimidazol-2-one,
4-fluoro-1,3-dihydro-2H-benzimidazol-2-one,
5-fluoro-1,3-dihydro-2H-benzimidazol-2-one,
6-fluoro-1,3-dihydro-2H-benzimidazol-2-one,
5-bromo-1,3-dihydro-2H-benzimidazol-2-one,
4-hydroxy-1,3-dihydro-2H-benzimidazol-2-one, 5-hydroxy-1,3-dihydro-2H-benzimidazol-2-one,
6-hydroxy-1,3-dihydro-2H-benzimidazol-2-one,
5-methyl-1,3-dihydro-2H-benzimidazol-2-one,
4-methylsulfonyl-1,3-dihydro-2H-benzimidazol-2-one,
4-(2-hydroxyethyl)-1,3-dihydro-2H-benzimidazol-2-one,
5-(2-hydroxyethyl)-1,3-dihydro-2H-benzimidazol-2-one,
4-aminomethyl-1,3-dihydro-2H-benzimidazol-2-one,
5-aminomethyl-1,3-dihydro-2H-benzimidazol-2-one,
4-methylsulfinylmethyl-1,3-dihydro-2H-benzimidazol-2-one,
5-methylsulfinylmethyl-1,3-dihydro-2H-benzimidazol-2-one,
4-methylsulfonylmethyl-1,3-dihydro-2H-benzimidazol-2-one,
4-ethylsulfonylmethyl-1,3-dihydro-2H-benzimidazol-2-one, and
4-(methoxycarbonylamino)methyl-1,3-dihydro-2H-benzimidazol-2-one are particularly preferred.

E meaning oxygen atom or sulfur atom, oxygen atom is the preferred.

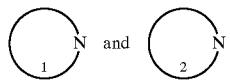

are same or different, and signify $C_3$–$C_9$ mono- or bi-cyclic aliphatic nitrogen-containing heterocyclic group(s) which may be substituted with halogen or lower alkyl.

links with the vicinal group which is expressed by

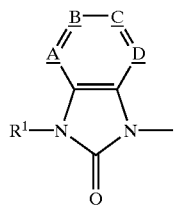

on a substitutable, optional ring carbon atom, and links with the group expressed by

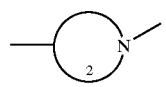

on a ring nitrogen atom.

links with the vicinal

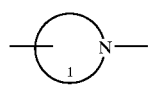

on a substitutable, optional ring carbon atom, and links with the group expressed by

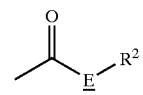

on a ring nitrogen atom.

"$C_3$–$C_9$ mono- or bi-cyclic aliphatic nitrogen-containing heterocyclic group(s) which may be substituted with halogen or lower alkyl" means named $C_3$–$C_9$ mono- or bi-cyclic aliphatic nitrogen-containing heterocyclic groups which are unsubstituted or named $C_3$–$C_9$ mono- or bi-cyclic aliphatic nitrogen-containing heterocyclic groups which have substituent(s) at their substitutable, optional position(s), one, two or more, preferably one or two, same or different substituents being selected from the group consisting of halogen and lower alkyl.

As the substituent halogen, for example, fluorine and chlorine atoms are preferred.

As the substituent lower alkyl, for example, methyl, ethyl and propyl groups are preferred.

As $C_3$–$C_9$ mono- or bi-cyclic aliphatic nitrogen-containing heterocyclic groups of

which may be same or different, for example, those groups represented by

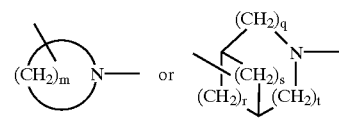

(in which m, q, r, s and t have the earlier given significations), more specifically, for example, azetidine-1,3-di-yl, piperidine-1,4-di-yl, hexahydroazepine-1,4-di-yl, 3-azabicyclo[3.3.0]octane-3,7-di-yl and 8-azabicyclo[3.2.1]octane-3,8-di-yl groups are preferred. In particular, piperidine-1,4-di-yl group is preferred.

Therefore, as

which may be same or different, for example, azetidine-1,3-di-yl, pyrrolidine-1,3-di-yl, piperidine-1,3-di-yl, piperidine-1,4-di-yl, 3-fluoropiperidine-1,4-di-yl, 4-methylpiperidine-1,4-di-yl, hexahydroazepine-1,3-di-yl, hexahydroazepine-1,4-di-yl, 3-azabicyclo[3.3.0]octane-3,7-di-yl and 8-azabicyclo[3.2.1]octane-3,8-di-yl groups are preferred. In particular, azetidine-1,3-di-yl, piperidine-1,4-di-yl, 3-fluoropiperidine-1,4-di-yl, 4-methyl-piperidine-1,4-di-yl, hexahydroazepine-1,4-di-yl, 3-azabicyclo[3.3.0]octane-3,7-di-yl and 8-azabicyclo[3.2.1]octane-3,8-di-yl groups are preferred. It is particularly preferred that both of

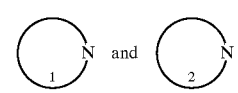

are piperidine-1,4-di-yl groups.

$R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino.

When $R^1$ is lower alkenyl, for example, vinyl, 1-propenyl, 2-propenyl and 3-methyl-2-butenyl groups are preferred.

When $R^1$ is lower alkynyl, for example, ethynyl and 2-propynyl groups are preferred.

When $R^1$ is cyclo (lower alkyl), for example, cyclopropyl, cyclobutyl and cyclopentyl groups are preferred.

When $R^1$ is lower alkanoyl, for example, acetyl and propionyl groups are preferred.

When $R^1$ is lower alkoxycarbonyl, for example, methoxycarbonyl, ethoxycarbonyl, propoxycarbonyl and isopropoxycarbonyl groups are preferred.

When $R^1$ is lower alkylcarbamoyl, for example, methylcarbamoyl and ethylcarbamoyl groups are preferred.

When $R^1$ is di(lower alkyl)carbamoyl, for example, dimethylcarbamoyl and diethylcarbamoyl groups are preferred.

When $R^1$ is lower alkylaminosulfonyl, for example, methylaminosulfonyl and ethylaminosulfonyl groups are preferred.

When $R^1$ is di(lower alkyl)aminosulfonyl, for example, dimethylaminosulfonyl and diethylaminosulfonyl groups are preferred.

"Lower alkylsulfonyl which may be substituted with halogen, hydroxyl or oxo" as $R^1$ means unsubstituted lower alkylsulfonyl groups as above-named, and those lower alkylsulfonyl groups having one or two or more, preferably one to three, substituents which may be same or different and are selected from the group consisting of halogen, hydroxyl and oxo, at their substitutable, oprional position(s).

As the substituent halogen, for example, fluorine atom is preferred.

As the "lower alkylsulfonyl" per se of said optionally substituted lower alkylsulfonyl, for example, methylsulfonyl, ethylsulfonyl, propylsulfonyl, isopropylsulfonyl and butylsulfonyl groups are preferred.

Therefore, as examples of those optionally substituted lower alkylsulfonyl, for example, methylsulfonyl, ethylsulfonyl, propylsulfonyl, isopropylsulfonyl, butylsulfonyl, fluoromethylsulfonyl, trifluoromethylsulfonyl, (2-hydroxyethyl)sulfonyl, (2-chloroethyl)sulfonyl, (2-oxopropyl)sulfonyl, (2,2,2-trifluoroethyl)sulfonyl and (3,3,3-trifluoropropyl)sulfonyl groups can be named. Of those, the preferred are methylsulfonyl, ethylsulfonyl, isopropylsulfonyl, butylsulfonyl, (2-hydroxyethyl)sulfonyl and (2,2,2-trifluoroethyl)sulfonyl groups, inter alia, methylsulfonyl group.

"Lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino" as $R^1$ means unsubstituted lower alkyl groups as above-named, and those lower alkyl groups having one, two or more, preferably one to three, substituents which may be same or different, at their substitutable, optional position(s), said substituent(s) being selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl) carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and, (di-lower alkylamino)sulfonylamino.

As the substituent halogen, for example, fluorine atom is preferred.

As the substituent cyclo (lower alkyl), for example, cyclopropyl and cyclobutyl groups are preferred.

As the substituent optionally fluorine-substituted lower alkoxy, for example, methoxy, ethoxy, propoxy, fluoromethoxy, difluoromethoxy and trifluoromethoxy groups are preferred.

As the substituent lower alkylamino, for example, methylamino and ethylamino groups are preferred.

As the substituent di(lower alkyl)amino, for example, dimethylamino and diethylamino groups are preferred.

As the substituent lower alkylthio, for example, methylthio and ethylthio groups are preferred.

As the substituent lower alkyl sulfinyl, for example, methylsulfinyl and ethylsulfinyl groups are preferred.

As the substituent lower alkylsulfonyl, for example, methylsulfonyl and ethylsulfonyl groups are preferred.

As the substituent lower alkoxycarbonyl, for example, methoxycarbonyl and ethoxycarbonyl groups are preferred.

As the substituent lower alkylcarbamoyl, for example, methylcarbamoyl and ethylcarbamoyl groups are preferred.

As the substituent di(lower alkyl)carbamoyl, for example, dimethylcarbamoyl and diethylcarbamoyl groups are preferred.

As the substituent lower alkylcarbamoyloxy, for example, methylcarbamoyloxy and ethylcarbamoyloxy groups are preferred.

As the substituent di(lower alkyl)carbamoyloxy, for example, dimethylcarbamoyloxy and diethylcarbamoyloxy groups are preferred.

As the substituent lower alkylaminosulfonyl, for example, methylaminosulfonyl and ethylaminosulfonyl groups are preferred.

As the substituent di(lower alkyl)aminosulfonyl, for example, dimethylaminosulfonyl and diethylaminosulfonyl groups are preferred.

As the substituent lower alkylsulfonylamino, for example, methylsulfonylamino and ethylsulfonylamino groups are preferred.

As the substituent (lower alkylcarbamoyl)amino, for example, (methylcarbamoyl)amino and (ethylcarbamoyl)amino groups are preferred.

As the substituent (di-lower alkylcarbamoyl)amino, for example, (dimethylcarbamoyl)amino and (diethylcarbamoyl)amino groups are preferred.

As the substituent (lower alkylamino)sulfonylamino, for example, (methylamino)sulfonylamino and (ethylamino) sulfonylamino groups are preferred.

As the substituent (di-lower alkylamino)sulfonylamino, for example, (dimethylamino)sulfonylamino and (diethylamino)sulfonylamino groups are preferred.

As the substituent(s) on $R^1$ lower alkyl, for example, cyano, halogen, hydroxyl, oxo, amino, cyclo(lower alkyl), optionally fluorine-substituted lower alkoxy, lower alkylamino, di(lower alkyl)amino, lower alkylthio, lower alkylsulfonyl, lower alkoxycarbonyl, carbamoyloxy, lower alkylsulfonylamino, (di-lower alkylcarbamoyl)amino, (lower alkylamino)sulfonylamino and (di-lower alkylamino)sulfonylamino groups are preferred.

As $R^1$ lower alkyl, for example, methyl, ethyl, propyl, isopropyl, butyl and isobutyl groups are preferred.

Therefore, as those optionally substituted lower alkyl as $R^1$, for example, methyl, ethyl, propyl, isopropyl, butyl, isobutyl, cyanomethyl, 2-fluoroethyl, 2,2-difluoroethyl, 2,2,2-trifluoroethyl, 3,3,3-trifluoropropyl, 2-hydroxyethyl, 3-hydroxypropyl, 2-oxopropyl, 2-oxobutyl, 2-aminoethyl, cyclopropylmethyl, methoxymethyl, 2-methoxyethyl, 2-ethoxyethyl, 2-methylaminoethyl, 2-dimethylaminoethyl, 2-diethylaminoethyl, methylthiomethyl, 2-methylthioethyl, methylsulfonylmethyl, 2-methylsulfonylethyl, ethoxycarbonylmethyl, 2-(carbamoyloxy)ethyl, 2-(methylsulfonylamino)ethyl, 2-(dimethylcarbamoylamino)ethyl, 2-(methylaminosulfonylamino)ethyl and 2-[(dimethylaminosulfonyl)-amino]ethyl groups may be named. Of those, methyl, ethyl, propyl, isopropyl, butyl, isobutyl, 2-fluoroethyl, 2,2-difluoroethyl, 3,3,3-trifluoropropyl, 2-hydroxyethyl, 2-oxopropyl, 2-oxobutyl, 2-aminoethyl, cyclopropylmethyl, 2-ethoxyethyl, 2-methylaminoethyl, 2-dimethylamioethyl, methylthiomethyl, 2-methylthioethyl, methylsulfonylmethyl, 2-methylsulfonylethyl, ethoxycarbonylmethyl and 2-(carbamoyloxy)ethyl groups are preferred.

As $R^1$, for example, lower alkenyl, cyclo(lower alkyl), lower alkoxycarbonyl or carbamoyl; lower alkylsulfonyl which may be substituted with halogen, hydroxyl or oxo; and above optionally substituted lower alkyl groups are preferred. In particular, lower alkylsulfonyl which may be substituted with halogen, hydroxyl or oxo are preferred. More specifically, for example, 3-methyl-2-butenyl, cyclopropyl, cyclobutyl, cyclopentyl, ethoxycarbonyl, carbamoyl, methylsulfonyl, ethylsulfonyl, isopropylsulfonyl, butylsulfonyl, (2-hydroxyethyl)sulfonyl, (2,2,2-trifluoroethyl)sulfonyl, methyl, ethyl, propyl, isopropyl, butyl, isobutyl, 2-fluoroethyl, 2,2-difluoroethyl, 3,3,3-trifluoropropyl, 2-hydroxyethyl, 2-oxopropyl, 2-oxobutyl, 2-aminoethyl, cyclopropylmethyl, 2-ethoxyethyl, 2-methylaminoethyl, 2-dimethylaminoethyl, methylthiomethyl, 2-methylthioethyl, methylsulfonylmethyl, 2-methylsulfonylethyl, ethoxycarbonylmethyl and 2-(carbamoyloxy)ethyl groups are preferred. Of those, methyl, ethyl, propyl and methylsulfonyl groups, inter alia, methylsulfonyl, are particularly preferred.

$R^2$ signifies lower alkyl.

As $R^2$, for example, methyl, ethyl propyl and isopropyl, in particular, methyl and ethyl, are preferred.

As preferred embodiments of the compounds of the present invention, for example, those in which <u>A</u>, <u>B</u>, <u>C</u> and <u>D</u> are same or differrent and signify methine group(s) which may be substituted with halogen, hydroxyl, lower alkylsulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, lower alkylcarbamoyloxy, di(lower alkyl) carbamoyloxy, lower alkoxycarbonylamino, aminosulfonyl, lower alkylaminosulfonyl, di(lower alkyl)aminosulfonyl, (lower alkylamino)sulfonylamino and (di-lower alkylamino)sulfonylamino; both

are 1,4-piperidine-di-yl; and $R^1$ is a lower alkenyl, cyclo(lower alkyl), lower alkoxycarbonyl or carbamoyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl) carbamoyloxy, aminosulfonyl, lower alkylaminosulfonyl, di(lower alkyl)aminosulfonyl, lower alkylsulfonylamino, (lower alkylcarbamoyl amino, (di-lower alkylcarbamoyl) amino, (lower alkylamino)sulfonylamino and (di-lower alkylamino)sulfonylamino can be named.

As the compounds of the present invention, for example, specifically the following are preferred;

1-[1-(1-methoxycarbonylpiperidin-4-yl)piperidin-4-yl]-3-(2-propynyl)-1,3-dihydro-2H-benzimidazol-2-one.

1-[1-(1-methoxycarbonylpiperidin-4-yl)piperidin-4-yl]-3-(2-propenyl)-1,3-dihydro-2H-benzimidazol-2-one, 1-[1-(1-methoxycarbonylpiperidin-4-yl)piperidin-4-yl]-3-n-butyl-1,3-dihydro-2H-benzimidazol-2-one, 1-[1-(1-methoxycarbonylpiperidin-4-yl)piperidin-4-yl]-3-methyl-1,3-dihydro-2H-benzimidazol-2-one, 1-[1-(1-methoxycarbonylpiperidin-4-yl)piperidin-4-yl]-3-(2,2,2-trifluoroethyl)-1,3-dihydro-2H-benzimidazol-2-one, 1-[1-(1-methoxycarbonylpiperidin-4-yl)piperidin-4-yl]-3-(methoxycarbonylmethyl)-1,3-dihydro-2H-benzimidazol-2-one, 1-[1-(1-methoxycarbonylpiperidin-4-yl)piperidin-4-yl]-3-(2-oxopropyl)-1,3-dihydro-2H-benzimidazol-2-one, 1-[1-(1-methoxycarbonylpiperidin-4-yl)piperidin-4-yl]-3-(2-aminoethyl)-1,3-dihydro-2H-benzimidazol-2-one, 1-[1-(1-methoxycarbonylpiperidin-4-yl)piperidin-4-yl]-3-(dimethylaminosulfonyl)-1,3-dihydro-2H-benzimidazol-2-one, 1-[1-(1-methoxycarbonylpiperidin-4-yl)piperidin-4-yl]-3-ethyl-1,3-dihydro-2H-benzimidazol-2-one, 1-[1-(1-methoxycarbonylpiperidin-4-yl)piperidin-4-yl]-3-n-propyl-1,3-dihydro-2H-benzimidazol-2-one, 1-[1-(1-methoxycarbonylpiperidin-4-yl)piperidin-4-yl]-3-acetyl-1,3-dihydro-2H-benzimidazol-2-one, 1-[1-(1-methoxycarbonylpiperidin-4-yl)piperidin-4-yl]-3-(methylsulfonyl)-1,3-dihydro-2H-benzimidazol-2-one, 1-[1-(1-methoxycarbonylpiperidin-4-yl)piperidin-4-yl]-3-(methoxycarbonyl)-1,3-dihydro-2H-benzimidazol-2-one, 1-[1-(1-methoxycarbonylazetidin-3-yl)piperidin-4-yl]-3-(methylsulfonyl)-1,3-dihydro-2H-benzimidazol-2-one, 1-[1-(1-methoxycarbonylpiperidin-4-yl)azetidin-3-yl]-3-(methylsulfonyl)-1,3-dihydro-2H-benzimidazol-2-one, 1-[1-(1-methoxycarbonylpiperidin-4-yl)piperidin-4-yl]-5-methyl-3-(methylsulfonyl)-1,3-dihydro-2H-benzimidazol-2-one,
1-[1-(1-methoxycarbonylpiperidin-4-yl)piperidin-4-yl]-4-fluoro-3-(methylsulfonyl)-1,3-dihydro-2H-benzimidazol-2-one,
1-[1-(1-methoxycarbonylpiperidin-4-yl)piperidin-4-yl]-3-(methylsulfonyl)-1,3-dihydro-2H-imidazo[4,5-b]pyridin-2-one,
1-[1-(1-ethoxycarbonylpiperidin-4-yl)piperidin-4-yl]-3-(methylsulfonyl)-1,3-dihydro-2H-benzimidazol-2-one,
1-[1-(1-methoxycarbonylpiperidin-4-yl)piperidin-4-yl]-3-(2-fluoroethyl-1,3-dihydro-2H-benzimidazol-2-one,
1-[1-(1-methoxycarbonylpiperidin-4-yl)piperidin-4-yl]-3-(2,2-difluoroethyl)-1,3-dihydro-2H-benzimidazol-2-one,
1-[1-(1-methoxycarbonylpiperidin-4-yl)piperidin-4-yl]-3-(3,3,3-trifluoropropyl)-1,3-dihydro-2H-benzimidazol-2-one,
1-[1-(1-methoxycarbonylpiperidin-4-yl)piperidin-4-yl]-3-(2-hydroxyethyl)-1,3-dihydro-2H-benzimidazol-2-one,
1-[1-(1-methoxycarbonylpiperidin-4-yl)piperidin-4-yl]-3-prenyl-1,3-dihydro-2H-benzimidazol-2-one,
1-[1-(1-methoxycarbonylpiperidin-4-yl)piperidin-4-yl]-3-(ethylsulfonyl)-1,3-dihydro-2H-benzimidazol-2-one,
1-[1-(1-methoxycarbonylpiperidin-4-yl)piperidin-4-yl]-3-(isopropylsulfonyl)-1,3-dihydro-2H-benzimidazol-2-one,
1-[1-(1-methoxycarbonylpiperidin-4-yl)piperidin-4-yl]-3-(n-butylsulfonyl)-1,3-dihydro-2H-benzimidazol-2-one,
1-[1-(1-methoxycarbonylpiperidin-4-yl)piperidin-4-yl]-3-carbamoyl-1,3-dihydro-2H-benzimidazol-2-one,
1-[1-(1-methoxycarbonylpiperidin-4-yl)piperidin-4-yl]-3-(ethoxycarbonylmethyl)-1,3-dihydro-2H-benzimidazol-2-one,
1-[1-(1-methoxycarbonylpiperidin-4-yl)piperidin-4-yl]-3-(2-oxo-n-butyl)-1,3-dihydro-2H-benzimidazol-2-one,
1-[1-(1-methoxycarbonylpiperidin-4-yl)piperidin-4-yl]-3-(methylsulfonylmethyl)-1,3-dihydro-2H-benzimidazol-2-one,
1-[1-(1-methoxycarbonylpiperidin-4-yl)piperidin-4-yl]-3-(methylthiomethyl)-1,3-dihydro-2H-benzimidazol-2-one,
1-[1-(1-methoxycarbonylpiperidin-4-yl)piperidin-4-yl]-3-(2-methylsulfonylethyl)-1,3-dihydro-2H-benzimidazol-2-one,
1-[1-(1-methoxycarbonylpiperidin-4-yl)piperidin-4-yl]-3-(2-methylthioethyl)-1,3-dihydro-2H-benzimidazol-2-one,
1-[1-(1-methoxycarbonylpiperidin-4-yl)piperidin-4-yl]-3-(2-ethoxyethyl)-1,3-dihydro-2H-benzimidazol-2-one,
1-[1-(1-ethoxycarbonylpiperidin-4-yl)piperidin-4-yl]-3-methyl-1,3-dihydro-2H-benzimidazol-2-one,
1-[1-(1-methoxycarbonylpiperidin-4-yl)piperidin-4-yl]-3-methyl-4-(methylsulfonyl)-1,3-dihydro-2H-benzimidazol-2-one,
1-[1-(1-methoxycarbonylpiperidin-4-yl)piperidin -4-yl]-3-methyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(ethylsulfonylmethyl)-1,3-dihydro-2H-benzimidazol-2-one,
1-[1-(1-methoxycarbonylpiperidin-4-yl)piperidin-4-yl]-3-methyl-4-(methoxycarbonylamino)methyl-1,3-dihydro-2H-benzimidazol-2-one
1-[1-(1-methoxycarbonylpiperidin-4-yl)piperidin-4-yl]-3-ethyl-4-(methoxycarbonylamino)methyl-1,3-dihydro-2H-benzimidazol-2-one,
1-[1-(1-methoxycarbonylpiperidin-4-yl)piperidin-4-yl]-3-(methylsulfonyl)-4-hydroxy-1,3-dihydro-2H-benzimidazol-2-one,
1-[1-(1-methoxycarbonylpiperidin-4-yl)piperidin-4-yl]-3-(methylsulfonyl)-5-hydroxy-1,3-dihydro-2H-benzimidazol-2-one,
1-[1-(1-methoxycarbonylpiperidin-4-yl)piperidin-4-yl]-3-(methylsulfonyl)-6-hydroxy-1,3-dihydro-2H-benzimidazol-2-one,
1-[1-(1-methoxycarbonylpiperidin-4-yl)piperidin-4-yl]-3-(methylsulfonyl)-5-bromo-1,3-dihydro-2H-benzimidazol-2-one,
1-[1-(1-methoxycarbonylpiperidin-4-yl)piperidin-4-yl]-3-(methylsulfonyl)-5-fluoro-1,3-dihydro-2H-benzimidazol-2-one,
1-[1-(1-methoxycarbonylpiperidin-4-yl)piperidin-4-yl]-3-(methylsulfonyl)-6-fluoro-1,3-dihydro-2H-benzimidazol-2-one, and
1-[1-(1-ethoxycarbonylpiperidin-4-yl)piperidin-4-yl]-3-(ethoxycarbonyl)-1,3-dihydro-2H-benzimidazol-2-one.

Of those, particularly
1-[1-(1-methoxycarbonylpiperidin-4-yl)piperidin-4-yl]-3-methyl-1,3-dihydro-2H-benzimidazol-2-one,
1-[1-(1-methoxycarbonylpiperidin-4-yl)piperidin-4-yl]-3-(methoxycarbonylmethyl)-1,3-dihydro-2H-benzimidazol-2-one,
1-[1-(1-methoxycarbonylpiperidin-4-yl)piperidin-4-yl]-3-ethyl-1,3-dihydro-2H-benzimidazol-2-one,
1-[1-(1-methoxycarbonylpiperidin-4-yl)piperidin-4-yl]-3-n-propyl-1,3-dihydro-2H-benzimidazol-2-one,
1-[1-(1-methoxycarbonylpiperidin-4-yl)piperidin-4-yl]-3-(2-hydroxyethyl)-1,3-dihydro-2H-benzimidazol-2-one,
1-[1-(1-methoxycarbonylpiperidin-4-yl)piperidin-4-yl]-3-(2-aminoethyl)-1,3-dihydro-2H-benzimidazol-2-one,
1-[1-(1-methoxycarbonylpiperidin-4-yl)piperidin-4-yl]-3-(methoxycarbonyl)-1,3-dihydro-2H-benzimidazol-2-one,
1-[1-(1-methoxycarbonylpiperidin-4-yl)piperidin-4-yl]-3-(methylsulfonyl)-1,3-dihydro-2H-benzimidazol-2-one,
1-[1-(1-methoxycarbonylpiperidin-4-yl)piperidin-4-yl]-3-(ethylsulfonyl)-1,3-dihydro-2H-benzimidazol-2-one,
1-[1-(1-methoxycarbonylpiperidin-4-yl)piperidin-4-yl]-5-methyl-3-(methylsulfonyl)-1,3-dihydro-2H-benzimidazol-2-one,
1-[1-(1-methoxycarbonylpiperidin-4-yl)piperidin-4-yl]-4-fluoro-3-(methylsulfonyl)-1,3-dihydro-2H-benzimidazol-2-one,
1-[1-(1-methoxycarbonylpiperidin-4-yl)piperidin-4-yl]-3-(methylsulfonyl)-5-fluoro-1,3-dihydro-2H-benzimidazol-2-one,
1-[1-(1-methoxycarbonylpiperidin-4-yl)piperidin-4-yl]-3-(methylsulfonyl)-6-fluoro-1,3-dihydro-2H-benzimidazol-2-one,
1-[1-(1-methoxycarbonylpiperidin-4-yl)piperidin-4-yl]-3-(2-fluoroethyl)-1,3-dihydro-2H-benzimidazol-2-one,
1-[1-(1-methoxycarbonylpiperidin-4-yl)piperidin-4-yl]-3-(2,2-difluoroethyl)-1,3-dihydro-2H-benzimidazol-2-one,
1-[1-(1-methoxycarbonylpiperidin-4-yl)piperidin-4-yl]-3-methyl-4-(methylsulfonyl)-1,3-dihydro-2H-benzimidazol-2-one,
1-[1-(1-methoxycarbonylpiperidin-4-yl)piperidin-4-yl]-3-methyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(ethylsulfonylmethyl)-1,3-dihydro-2H-benzimidazol-2-one, 1-[1-(1-methoxycarbonylpiperidin-4-yl)piperidin-4-yl]-3-methyl-4-(methoxycarbonylamino)methyl-1,3-dihydro-2H-benzimidazol-2-one and 1-[1-(1-methoxycarbonylpiperidin-4-yl)piperidin-4-yl]-3-ethyl-4-(methoxycarbonylamino)methyl-1,3-dihydro-2H-benzimidazol-2-one are preferred.

The production methods of the compounds of the present invention are explained hereunder.

Those compounds of the present invention which are represented by the general formula [I] can be prepared, for example, by the production method 1, 2, 3 or 4 shown in the following.

Production Method 1

A compound represented by the general formula [I] or a salt thereof can be prepared by a process comprising reacting a compound of a general formula [II]

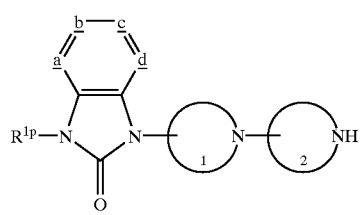

[II]

in which a, b, c and d are same or different and signify methine group(s) or nitrogen atom, said methine group(s) being optionally substituted with cyano, halogen, optionally protected hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxycarbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl)(lower alkyl)amino, (di-lower alkylaminosulfonyl)(lower alkyl)amino, and optionally protected hydroxyl, amino and lower alkylamino; $R^{1p}$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, optionally protected hydroxyl or oxo, or lower alkyl which may have a substituent selected from the group consisting of cyano, halogen, oxo, cyclo(lower alkyl), optionally fluoro-substituted lower alkoxy, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino, and optionally protected hydroxyl, amino and lower alkylamino; E

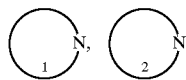

and $R^2$ have the earlier given significations] with a compound represented by a general formula [III]

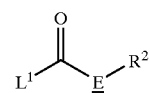

[III]

[in which $L^1$ signifies a leaving group; E and $R^2$ have the earlier given significations] to form a compound represented by a general formula [IV]

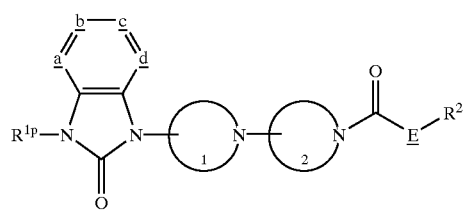

[IV]

[in which a, b, c, d, E,

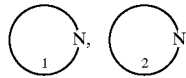

$R^{1p}$ and $R^2$ have the earlier given significations] and if necessary removing the protective group(s).

Examples of the leaving group $L^1$ include halogen atoms such as chlorine, bromine or iodine; organic sulfonyl groups such as methanesulfonyl, ethanesulfonyl and benzenesulfonyl; organic sulfonyloxy groups such as methanesulfonyloxy, trifluoromethanesulfonyloxy and p-toluenesulfonyloxy; and 1-imidazolyl group.

The reaction between a compound of the formula [II] and a compound of the formula [III] is usually conducted by using equimolar amounts of the two or using either one of them in slight molar excess, in an inert solvent which is not detrimental to the reaction.

As the inert solvent, for example, ethers such as tetrahydrofuran and dioxane; halogenated hydrocarbons such as methylene chloride and chloroform; and aprotic polar solvents such as dimethylformamide, N,N-dimethylacetamide and acetonitrile are preferred.

It is preferred to carry out the above reaction in the presence of a base. As the base, for example, organic bases such as triethylamine, diisopropylethylamine, pyridine, 4-dimethylaminopyridine and lithium diisopropylamide; or inorganic bases such as sodium hydride, sodium hydroxide, sodium carbonate, potassium carbonate and sodium hydrogencarbonate are preferred.

The use rate of the base is 1 mole or molar excess, preferably 1 to 3 moles, per mole of the compound represented by the general formula [II].

The reaction temperature is usually from −78° C. to 150° C., preferably from 0° C. to 80° C.

The reaction time is usually from 5 minutes to 7 days, preferably from 30 minutes to 24 hours.

After termination of the reaction, customary treatment(s) are conducted to provide crude product of a compound of the general formula [IV].

Where amino, hydroxyl or a like group(s) which do not participate in the reaction are present in the above reaction, such amino or hydroxyl groups are preferably protected with suitable amino- or hydroxyl-protective groups before conducting the reaction, which protective group(s) are removed after the reaction.

As amino-protective groups, for example, aralkyl groups such as benzyl, p-methoxybenzyl, 3,4-dimethoxybenzyl, o-nitrobenzyl, p-nitrobenzyl, benzhydryl and trityl; lower alkanoyl groups such as formyl, acetyl, propionyl, butyryl and pivaloyl; benzoyl; arylalkanoyl groups such as phenylacetyl and phenoxyacetyl; lower alkoxycarbonyl groups such as methoxycarbonyl, ethoxycarbonyl, propyloxycarbonyl and tert-butoxycarbonyl; aralkyloxycarbonyl groups such as benzyloxycarbonyl, p-nitrobenzyloxycarbonyl and phenethyloxycarbonyl; lower alkylsilyl groups such as trimethylsilyl and tert-butyldimethylsilyl; phthaloyl; and aralkylidene groups such as benzylidene, p-chlorobenzylidene and o-nitrobenzylidene may be named. In particular, acetyl, pivaloyl, benzoyl, ethoxycarbonyl and tert-butoxycarbonyl groups are preferred.

As hydroxyl-protective groups, for example, substituted silyl groups such as trimethylsilyl, tert-butyldimethylsilyl and tert-butyldiphenylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl and trityl; and acyl groups such as formyl and acetyl may be named. In particular, methoxymethyl, tetrahydropyranyl, trityl, trimethylsilylethoxymethyl, thert-butyldimethylsilyl and acetyl groups are preferred.

Where a compound represented by the general formula [IV] contains protected amino or hydroxyl group(s), a compound represented by the general formula [I] can be prepared therefrom by removing the protective group(s). Deprotection of said functional group(s) can be effected following a method known per se, for example, the method described in *Protective Groups in Organic Synthesis,* T. W. Greene, John Wiley & Sons, (1981) or a method analogous thereto such as, for example, solvolysis using an acid or a base, chemical reduction using metal hydride complex or the like, or catalytic reduction using palladium-on-carbon catalyst, Raney nickel catalyst or the like.

Production Method 2

A compound represented by the general formula [I] or a salt thereof can be prepared by a process comprising subjecting a compound of a general formula [V]

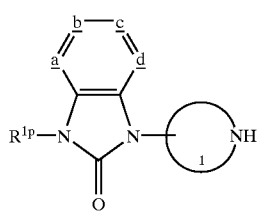

[V]

[in which $\underline{a}$, $\underline{b}$, $\underline{c}$, $\underline{d}$,

and $R^{1p}$ have the earlier given significations] and a compound of a general formula [VI]

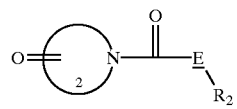

[VI]

[in which $\underline{E}$,

and $R^2$ have the earlier given significations] to a reducting aminaton reaction to form a compound of a general formula [IV]

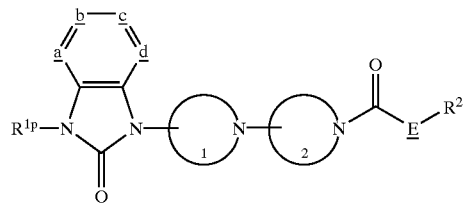

[IV]

[in which $\underline{a}$, $\underline{b}$, $\underline{c}$, $\underline{d}$, $\underline{E}$,

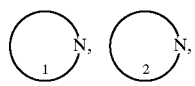

$R^{1p}$ and $R^2$ have the earlier given significations], and if necessary removing the protective group(s).

The reducing amination reaction between a compound of the formula [V] and a compound of the formula [VI] is usually conducted using equimolar amounts of the two or using either one of them in slight molar excess.

The reaction is usually conducted in an inert solvent. As the inert solvent, for example, alcohols such as methanol, ethanol, propanol and 2-propanol; ethers such as ethyl ether, tetrahydrofuran and dioxane; halogenated hydrocarbons such as methylene chloride, chloroform and 1,2-dichloroethane; aromatic hydrocarbons such as benzene, toluene, chlorobenzene and xylene; aprotic polar solvents such as dimethylformamide, ethyl acetate, acetonitrile and hexamethylphosphoric triamide; and mixtures of the foregoing may be named.

The reaction temperature is usually from 0° C. to the boiling point of used solvent, preferably from room temperature to 100° C.

The reaction time usually ranges from 5 minutes to 48 hours, preferably from 10 minutes to 24 hours.

After termination of the above reaction, the reaction liquid may be used in the subsequent reducing reaction as it is or distilled off, or a compound which is expressed by a general formula [X]

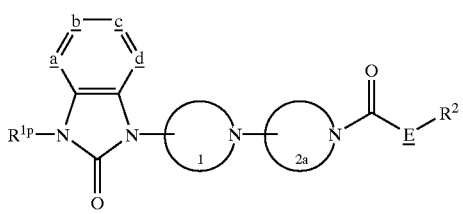

[X]

[in which

signifies a $C_3$–$C_9$ mono- or bi-cyclic aliphatic nitrogen-contaiing heterocyclic group which is optionally substituted with halogen or lower alkyl and which has a double bond between the ring carbon binding with

and another ring carbon adjacent to said carbon; and a, b, c, E,

$R^{1p}$ and $R^2$ have the earlier given significations] is isolated by using customary separation means and subjected to the subsequent reducing reaction.

Said reducing reaction can be performed by using, for example, metal hydride complex such as lithium borohydride, sodium borohydride, sodium cyanoborohydride, sodium triacetoxyborohydride, lithium aluminum hydride and the like, or by catalytic reduction using, for example, palladium-on-carbon catalyst, Raney-nickel catalyst and the like.

In particular, when a reducing agent which predominantly reduces imine/enamine, such as sodium cyanoborohydride, sodium triacetoxyborohydride or the like is used, the reaction liquid can be subjected to the reducing reaction as it is, without isolating the compound represented by the general formula [IX].

Where a metal hydride complex is used as the reducing agent, the use rate of the reducing agent usually ranges from 1 mole to molar excess, preferably from 1 to 5 moles, per mole of said imine.

In said reducing reaction, depending on the kind of reducing agent used, suitably a solvent may be used, for example, an inert solvent selected from alcohols such as methanol and ethanol; ethers such as dimethyl ether, ethyl ether, diisopropyl ether, dibutyl ether, dimethoxyethane, dioxane, tetrahydrofuran and diglyme; halogenated hydrocarbons such as methylene chloride, chloroform and dichloroethane; aliphatic hydrocarbons such as pentane, hexane, heptane and cyclohexane; aromatic hydrocarbons such as benzene and toluene; and their mixtures.

The reaction temperature usually ranges from −20° C. to 100° C., preferably from 0° C. to room temperature.

The reaction time usually ranges from 5 minutes to 7 days, preferably from 1 to 6 hours.

Furthermore, the hydrogen pressure in the catalytic reducing reaction is preferably from atmospheric to 5 atmospheres, and the use rate of the catalyst usually ranges from 1/100 to 1, preferably from 1/100 to 1/10, per 1 of the starting compound [X], by weight.

After termination of the reaction, customary treatment(s) are conducted to provide crude product of a compound of the general formula [IV].

Where amino, hydroxyl or like group(s) which do not participate in the reaction are present in the above reaction, such amino or hydroxyl groups are preferably protected with a suitable amino- or hydroxyl-protective groups before conducting the reaction, which protective group(s) are removed after the reaction.

Where a compound represented by the formula [IV] contains protected amino or hydroxyl group(s), a compound represented by the general formula [I] can be prepared therefrom by removing the protective group(s).

As for the amino- or hydroxyl-protective groups and the deprotection, those protective groups and deprotection means as described in connection with the production method 1 are applicable.

Production Method 3

A compound represented by the general formula [I] or a salt thereof can be prepared by a process comprising reacting a compound represented by a general formula [VII]

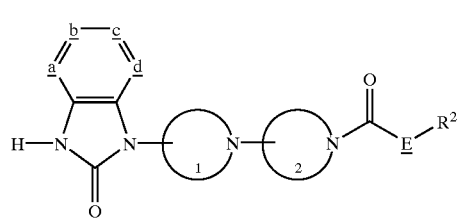

[VII]

[in which a, b, c, d, E,

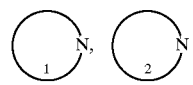

and $R^2$ have the earlier given significations] with a compound represented by a general formula [VIII]

$R^{1p}$—$L^2$ [VIII]

[in which $L^2$ signifies a leaving group, and $R^{1p}$ has the earlier given signification], to form a compound represented by the general formula [IV]

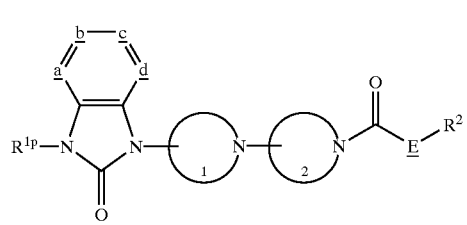

[IV]

[in which a, b, c, d, E,

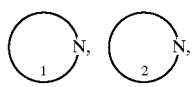

R$^{1p}$ and R$^2$ have the earlier given significations] and if necessary removing protective group(s).

As the leaving groups indicated as L$^2$, those leaving groups as exemplified for the leaving group L$^1$ can be named.

The reaction of a compound of the general formula [VII] with a compound of the general formula [VIII] can be performed in the analogous manner to that of a compound of the general formula [II] with a compound of the general formula [III] as in the production method 1, applying similar reaction conditions and other features.

After termination of the reaction, customary treatment(s) are conducted to provide crude product of a compound of the general formula [IV].

Where amino, hydroxyl or a like group(s) which do not participate in the reaction are present in the above reaction, such amino or hydroxyl groups are preferably protected with suitable amino- or hydroxyl-protective groups before conducting the reaction, which protective group(s) are removed after the reaction.

Where a compound represented by the formula [IV] contains protected amino or hydroxyl group(s), a compound represented by the general formula [I] can be prepared therefrom by removing the protective group(s).

As for the amino- or hydroxyl-protective groups and the deprotection, those protective groups and deprotection means as described in connection with the production method 1 are applicable.

Production Method 4

A compound represented by the general formula [I] or a salt thereof can be prepared by a process comprising reacting a compound. of a general formula [IX]

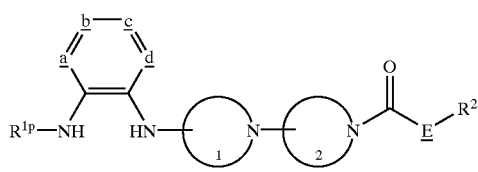

[IX]

[in which a, b, c, d, E,

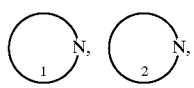

is R$^{1p}$ and R$^2$ have the earlier given significations], with a compound selected from the group consisting of carbonyldiimidazole, triphosgene, diphosgene, methyl chloroformate, ethyl chloroformate, dimethyl carbonate and diethyl carbonate, to form a compound represented by the general formula [IV],

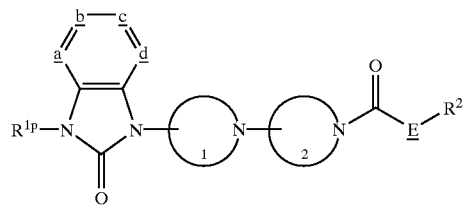

[IV]

[in which a, b, c, d, E,

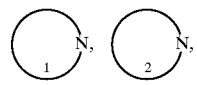

R$^{1p}$ and R$^2$ have the earlier given significations], and if necessary removing protective group(s).

The reaction of a compound of the general formula [IX] with a compound selected from the group consisting of carbonyldiimidazole, triphosgene, diphosgene, methyl chloroformate, ethyl chloroformate, dimethyl carbonate and diethyl carbonate is usually conducted using a chemical equivalent or excessive amount of the compound selected from the group consisting of carbonyldiimidazole, triphosgene, diphosgene, methyl chloroformate, ethyl chloroformate, dimethyl carbonate and diethyl carbonate, to the compound of the general formula [IX].

This reaction may be conducted in the presence of a base, if necessary, preferred examples of the base including organic bases such as triethylamine, diisopropylethylamine and 4-dimethylaminopyridine; and inorganic bases such as sodium hydride, sodium carbonate, potassium carbonate and sodium hydrogenecarbonate.

The reaction is usually conducted in an inert solvent, examples of the inert solvent including alcohols such as methanol, ethanol, propanol and 2-propanol; ethers such as ethyl ether, tetrahydrofuran and dioxane; halogenated hydrocarbons such as methylene chloride, chloroform and 1,2-dichloroethane; aromatic a hydrocarbons such as benzene, toluene, chlorobenzene and xylene; aprotic polar solvents such as dimethylformamide, ethyl acetate, acetonitrile and hexamethylphosphoric triamide; and mixtures of the foregoing.

The reaction temperature is usually from 0° C. to the boiling point of used solvent, preferably from room temperature to 100° C.

The reaction time usually ranges from 5 minutes to 48 hours, preferably from 10 minutes to 24 hours.

After termination of the reaction, customary treatment(s) are conducted to provide crude product of a compound of the general formula [IV].

Where amino, hydroxyl or a like group(s) which do not participate in the reaction are present in the above reaction, such amino or hydroxyl groups are preferably protected with suitable amino- or hydroxyl-protective groups before conducting the reaction, which protective group(s) are removed after the reaction.

Where a compound represented by the formula [IV] contains protected amino or hydroxyl group(s), a compound represented by the general formula [I] can be prepared therefrom by removing the protective group(s).

As for the amino- or hydroxyl-protective groups and the deprotection, those protective groups and deprotection means as described in connection with the production method 1 are applicable.

Isolation and purification of those compounds expressed by the general formula [I], [IV] or [X], which are obtained by the above-described methods, can be accomplished by customary separation means such as column chromatography using silica gel, adsorption resin and the like, liquid column chromatography, solvent extraction or recrystallization, reprecipitation and the like, conducted either singly or in combination.

Those compounds expressed by the general formula [I] can be converted to pharmaceutically acceptable salts by conventional means. Conversely, conversion from such salts to free compounds can be performed by conventional means.

As those compounds expressed by the general formulae [II], [III], [V], [VI], [VII], [VIII] or [IX] and other starting compounds, for example, commercially available ones may be used, or they can be prepared by methods taught in literature [e.g., see Tetrahedron, Vol.54, p.487 (1998); International Publication WO96/13262; Protective Groups in Organic Synthesis, T. W. Greene, John Wiley & Sons (1981)], methods analogous thereto or those described in working or referential examples.

Usefulness of compounds of the present invention is proven, for example, by the following pharmacological test esxamples.

Pharmacological Test 1 (in vitro Function Assay)

cDNA which codes a human m4 receptor gene [cf. Science, Vol.237, pp.527–532 (1987)] was cloned into an expression vector pcDNA3 (Invitrogen Co.) in which the promoter was modified to human EF-1a, to prepare pEFcDNA3/hm4. Also cDNA which codes a-subunit gene of GTP-bound protein Gi2 was cloned into an expression vector pIRESpuro (CLONTECH Co.) to prepare pIRESpuro/Gi. Then pEFcDNA3/hm4 and pIRES puro/Gi were introduced into CHO cells, together with pCRE-Luc (CLONTECH Co.) and pcDNAhyg (Invitrogen Co.), to provide a stable strain (hm4/Gi/Luc/CHO) which was resistant to selective drugs G418, puromysin and hygromysin B for selection.

This cell strain was cultured overnight to confluent in 96 well view plate (PACKARD CO.).

This cell strain was loaded with calcium indicator Fluo-3 acetoxymethyl ester (Molecular Probes Co.), then the intracellular calcium concentration was measured by transient increase in intracellular fluorescence intensity, elicited by each test compound in the presence of ATP (10 nM), using FLIPR™ (Molecular Device Co.). The maximum intracellular fluorescence intensity of each test compound (10 mm) was determined as % agonist activity, the rise in the intracellular fluorescence intensity elicited by carbachol (10 mm) as the control drug being set as 100% value. The results are shown in Table 1.

TABLE 1

| M4 Receptors-Stimulating Activity | |
|---|---|
| Compound | Agonist Activity (%) |
| Example 1 | 91 |
| Example 2 | 96 |
| Example 3 | 101 |
| Example 4 | 96 |
| Example 5 | 90 |
| Example 6 | 92 |
| Example 7 | 97 |
| Example 8 | 95 |
| Example 10 | 94 |
| Example 11 | 101 |

TABLE 1-continued

| M4 Receptors-Stimulating Activity | |
|---|---|
| Compound | Agonist Activity (%) |
| Example 12 | 95 |
| Example 13 | 95 |
| Example 14 | 95 |
| Example 20 | 94 |

From the above, it is demonstrated that the compounds of the present invention possess M4 receptors-stimulating action.

Pharmacological Test 2 (Mouse Tail Pinch Test)

Analgesic action of compounds of the invention was evaluated by tail pinch method (Haffner method). In the test, male mice of ICR strain (5–6 weeks old, Nippon SLC Co.). Root protions of mice' tails were pinched with an arterial Kle mme, and latency until each mouse bit at the Kle mme was measured. The analgetic effect was recorded based on the following equation. For preventing tissue damage, the cut-off time was set to be 6 seconds. The analgesic effect was calculated according to the following equation:

Analgesic effect (%)=[(Latency after drug administration–latency before drug administration)/(cut-off time 6 seconds–latency before drug administration)]×100.

Test compounds were subcutaneously administered at a dosage of 1 mg/kg each, and their analgetic action was examined according to the above-described method. In consequence, for example, as for the compounds of Examples 4, 10, 11, 13 and 14, 18%–100% analgetic effect was observed.

From the above results, compounds of the present invention are found to stimulate muscarinic acetylcholine receptors M4 and are useful as, for example, analgesics for diseases accompanying pain such as cancerous pain, post-operative pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis.

Those compounds represented by the general formula [I] can be administered orally or parenterally, and when they are formulated into preparation forms suitable for such administration, they can be offered as, for example, analgesic or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis. In clinical use of compounds of the present invention, it is also possible to add pharmaceutically acceptable adjuvants in accordance with individual form of administration and formulate them into various preparation forms before administration. As adjuvants in such occasions, various adjuvants customarily used in the field of pharmaceutical preparations can be used, which include, for example, gelatin, lactose, white sugar, titanium dioxide, starch, crystalline cellulose, hydroxypropylmethyl cellulose, carboxymethyl cellulose, corn starch, microcrystalline wax, white vaseline, magnesiu mmetasilicate aluminate, anhydrous calcium phosphate, citric acid, trisodium citrate, hydroxypropyl cellulose, sorbitol, sorbitan fatty acid esters, polysorbate, sucrose fatty acid esters, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropyl cyclodextrin.

The forms of the pharmaceutical preparations obtained in the form of the mixtures with these adjuvants include solid pharmaceutical preparations such as, for example, tablets, capsules, granules, powders and suppositories; and liquid pharmaceutical preparations such as, for example, syrups, elixirs and parenteral solutions, and they can be prepared according to conventional methods in the pharmaceutical preparation field. In the case of the liquid pharmaceutical preparations, they may be dissolved or suspended in water or other suitable media at the time of use. Furthermore, particularly in the case of the parenteral solutions, they may be dissolved or suspended, if necessary, in a physiological saline solution or a glucose solution, and a buffer or a preservative may also be added.

These pharmaceutical preparations can contain the compounds of the present invention in a proportion of 0.1 to 100% by weight, preferably 0.1 to 50% by weight based on the whole pharmaceutical components. These pharmaceutical preparations may contain other compounds which are therapeutically active.

When the compounds of the present invention are used as analgesic or agents for treating tolerance to a narcotic analgesics represented by morphine, dependence on a narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis, their dosages and administration frequency differ depending on sex, age, body weight and conditions of individual patients and also on the kind and extent of intended therapeuric effect. In general, for oral administration it is preferred to administer 0.01–10 mg/kg/day for adult in single or divided doses, and for parenteral administration, 0.003–3 mg/kg/day, in single or divided doses. Depending on patient's conditions, prophylactic administration is permissible.

Best Mode for Carrying Out the Invention

The present invention is more specifically explained, referring to working examples and referential examples, which should not be construed to restrict the scope of the invention in any way.

EXAMPLE 1

Preparation of 1-[1-(1-methoxycarbonylpiperidin-4-yl)-piperidin-4-yl]-3-(2-propinyl)-1,3-dihydro-2H-benzimidazol-2-one 1-[1-(1-Methoxycarbonylpiperidin-4-yl)piperidin-4-yl]-1,3-di-hydro-2H-benzimidazol-2-one (28 mg) as synthesized by the method of Referential Example 1 was dissolved in 5 ml of dimethylformamide, and to which 2.0 mg of sodium hydride was added under cooling with ice, followed by 30 minutes' stirring. Ten(10) mg of propargyl bromide was added to the reaction liquid which was stirred for further 3 hours at room temperature. After adding saturated aqueous sodium bicarbonate solution and concentrating the reaction liquid, the resulting residue was distributed between saturated aqueous sodium bicarbonate solution and chloroform. The organic layer was dried over anhydrous sodium sulfate, concentrated, and the resulting residue was purified by silica gel column chromatography (chloroform/methanol=20/1). Thus 11.3 mg of the title compound was obtained as a colorless oil.

$^1$H-NMR(CDCl$_3$) δ:1.42–1.55(2H, m),1.76–1.90(4H, m), 2.26–2.30(1H, m), 2.31–2.58(5H, m),2.77(2H, brt, J=11.7 Hz), 3.04 (2H, brd, J=6.6Hz), 3.69(3H, s), 4.10–4.43(3H, m), 4.68 (2H, d, J=2.0 Hz), 7.03–7.40(4H, m)

ESI-MS*(M+H)$^+$: 397

*electrospray-ionizing mass spectrometry, which was the same in all of the following examples

EXAMPLE 2

Preparation of 1-[1-(1-methoxycarbonylpiperidin-4-yl)-piperidin-4-yl]-3-(2-propenyl)-1,3-dihydro-2H-benzimidazol-2-one Example 1 was repeated except that the propargyl bromide was replaced with allyl iodide, and the title compound was obtained as a colorless oil.

$^1$H-NMR(CDCl$_3$) δ:1.38–1.56(2H, m), 1.76–1.92(5H, m), 2.30–2.60 (4H, m), 2.77(2H, brt, J=12.6 Hz), 2.98–3.08 (2H, m), 3.69(3H, s), 4.05–4.47(3H, m), 4.47–4.53(2H, m), 5.17–5.21(1H, m), 5.22–5.25(1H, m), 5.82–5.97(1H, m), 6.93–7.14(3H, m), 7.20–7.38(1H, m)

ESI-MS(M+H)$^+$: 399

EXAMPLE 3

Preparation of 1-[1-(1-methoxycarbonylpiperidin-4-yl)-piperidin-4-yl]-3-n-butyl-1,3-dihydro-2H-benzimidazol-2-one Example 1 was repeated except that the propargyl bromide was replaced with n-butyl iodide, and the title compound was obtained as a colorless oil.

$^1$H-NMR(CDCl$_3$) δ:1.40(2H, sept, J=7.9 Hz), 1.45(1H, dt, J=2.6 Hz, 13.3 Hz), 1.49(1H, dt, J=2.6 Hz, 13.3 Hz), 1.70–2.02 (4H, m), 1.72(2H, quint, J=7.6 Hz), 2.30–2.58 (5H, m), 2.77(2H, brt, J=11.9 Hz), 3.04 (2H, brd, J=6.9 Hz), 3.69(3H, s), 3.86(2H, t, J=7.0 Hz), 4.08–4.44 (3H, m), 6.96–7.10(3H, m), 7.26–7.32(1H, m)

ESI-MS(M+H)$^+$: 415

EXAMPLE 4

Preparation of 1-[1-(1-methoxycarbonylpiperidin-4-yl)-piperidin-4-yl]-3-methyl-1,3-dihydro-2H-benzimidazol-2-one Example 1 was repeated except that the propargyl bromide was replaced with methyl iodide, and the title compound was obtained as a colorless oil.

$^1$H-NMR(CDCl$_3$) δ:1.45(1H, dt, J=3.9 Hz, 12.3 Hz), 1.49(1H, dt, J=3.9 Hz, 11.8 Hz), 1.72–1.91(5H, m), 2.29–2.58(4H. m), 2.78(2H, brt, J=12.6 Hz), 3.04 (2H, brd, J=12.6 Hz), 3.41(3H, s), 3.69(3H, s), 4.05–4.46 (3H, m), 6.95–7.00(1H, m), 7.05(1H, dd, J=1.6 Hz, 4.3 Hz), 7.08(1H, dd, J=1.9 Hz, 4.0 Hz),7.26–7.32(1H, m)

ESI-MS(M+H)$^+$: 373

EXAMPLE 5

Preparation of 1-[1-(1-methoxycarbonylpiperidin-4-yl)-piperidin-4-yl]-3-(2,2,2-trifluoroethyl)-1,3-dihydro-2H-benzimidazol-2-one Example 1 was repeated except that the propargyl bromide was replaced with (2,2,2-trifluoroethyl) iodide, and the title compound was obtained as a colorless oil.

$^1$H-NMR(CDCl$_3$) δ:1.18–1.40(2H, m), 1.75–1.92(4H, m), 2.20–2.60 (5H,m), 2.77(2H, brt, J=11.4 Hz), 3.05 (2H, brd, J=7.2 Hz), 3.69(3H,s), 4.08–4.52(3H, m), 4.45 (2H, q, J=8.4Hz), 7.02–7.18(3H, m), 7.18–7.38(1H, m)

ESI-MS(M+H)⁺: 441

EXAMPLE 6

Preparation of 1-[1-(1-methoxycarbonylpiperidin-4-yl)-piperidin-4-yl]-3-(methoxycarbonylmethyl)-1,3-dihydro-2H-benzimidazol-2-one Example 1 was repeated except that the propargyl bromide was replaced with methyl bromoacetate, and the title compound was obtained as a pale yellow oil.

¹H-NMR(CDCl₃) δ:1.45(1H, dt, J=4.4 Hz, 11.9 Hz), 1.49 (1H, dt, J=4.4H, 11.9 Hz), 1.73–1.98(4H, m), 2.30–2.59 (5H, m),2.77(2H, brt, J=11.9 Hz), 3.05(2H, brd, J=7.6 Hz), 3.69(3H, s),3.76(3H, s),4.08–4.44(3H, m), 4.63(2H, s), 6.84–6.92(1H, m), 7.02–7.11(2H, m),7.26–7.29(1H, m)

ESI-MS(M+H)⁺: 431

EXAMPLE 7

Preparation of 1-[1-(1-methoxycarbonylpiperidin-4-yl)-piperidin-4-yl]-3-(2-oxopropyl)-1,3-dihydro-2H-benzimidazol-2-one Example 1 was repeated except that the propargyl bromide was replaced with 1-(methanesulfonyloxy)acetone which was prepared by the method of Referential Example 2, and the title compound was obtained as a pale yellow oil.

¹H-NMR(CDCl₃) δ:1.45(1H, dt, J=3.9Hz, 11.7 Hz), 1.49 (1H, dt, J=3.9 Hz, 11.7 Hz), 1.70–1.94(4H, m), 2.21(3H, s), 2.30–2.60(5H, m), 2.52(2H, brt, J=11.5 Hz), 3.05 (2H, brd, J=7.6 Hz), 3.69(3H, s),4.08–4.43(3H, m),4.61 (2H, s), 6.75–6.85(1H, m), 6.98–7.15(2H, m),7.20–7.35(1H, m)

ESI-MS(M+H)⁺: 415

EXAMPLE 8

Preparation of 1-[1-(1-methoxycarbonylpiperidin-4-yl)-piperidin-4-yl]-3-(2-aminoethyl)-1,3-dihydro-2H-benzimidazol-2-one Example 1 was repeated except that the propargyl bromide was replaced with 2-[bis(tert-butoxycarbonyl)amino] ethyl bromide, and from 40 mg of 1-[1-(1-methoxycarbonylpiperidin-4-yl)piperidin-4-yl]-1,3-dihydro-2H-benzimidazol-2-one, 51 mg of 1-[1-(1-methoxycarbonylpiperidin-4-yl)piperidin-4-yl]-3-{2-[bis(tert-butoxycarbonyl)-amino]ethyl}-1,3-dihydro-2H-benzimidazol-2-one was obtained. To this compound 5 ml of trifluoroacetic acid was added, stirred for 30 minutes at room temperature and the trifluoroacetic acid was distilled off. The residue was distributed between 0.5N sodium hydroxide solution and chloroform, and the organic layer was dried over anhydrous sodium sulfate and concentrated. The resulting residue was purified by alumina column chromatography (chloroform/methanol=49/1) to provide 22.3 mg of the title compound as a yellow-tinted oil.

¹H-NMR(CDCl₃) δ:1.45(1H, dt, J=4.3 Hz, 11.7 Hz), 1.49 (1H, dt, J=4.0 Hz, 11.4 Hz), 1.75–1.93(4H, m), 2.31–2.58 (5H, m), 2.78(2H, brt, J=12.3 Hz), 2.98–3.13(2H, m), 3.07 (2H, t, J=5.9 Hz), 3.69(3H, s), 3.94(2H, t, J=6.3 Hz), 4.20 (2H, brs), 4.28–4.42(1H, m), 7.01–7.09(3H, m), 7.24–7.28 (1H, m)

ESI-MS(M+H)⁺: 402

EXAMPLE 9

Preparation of 1-[1-(1-methoxycarbonylpiperidin-4-yl)-piperidin-4-yl]-3-(dimethylaminosulfonyl)-1,3-dihydro-2H-benzimidazol-2-one Example 1 was repeated except that the propargyl bromide was replaced with dimethylsulfamoyl chloride, and the title compound was obtained as yellow-tinted oil.

¹H-NMR(CDCl₃) δ:1.44(1H, dt, J=4.0 Hz, 12.1 Hz), 1.48(1H,dt,J=4.0 Hz, 12.1 Hz), 1.74–1.87(4H, m), 2.30–2.58 (5H, m), 2.77(2H, brt, J=11.7 Hz), 2.99–3.12(2H, m), 3.08 (6H, s), 3.69(3H, s), 4.10–4.35(3H, m), 7.06–7.19 (2H, m), 7.21–7.31(1H, m), 7.73–7.79(1H, m)

ESI-MS(M+H)⁺: 466

EXAMPLE 10

Preparation of 1-[1-(1-methoxycarbonylpiperidin-4-yl)-piperidin-4-yl]-3-ethyl-1,3-dihydro-2H-benzimidazol-2-one Example 1 was repeated except that the propargyl bromide was replaced with ethyl iodide, and the title compound was obtained as a colorless oil.

¹H-NMR(CDCl₃) δ:1.33(3H, t, J=7.3 Hz), 1.45 (1H, dt, J=3.9 Hz, 11.2 Hz), 1.49(1H, dt, J=5.0 Hz, 11.2 Hz), 1.71–1.90(5H, m), 2.30–2.59(4H, m), 2.77 (2H, brt, J=12.2 Hz), 3.05(2H, brd, J=6.9 Hz), 3.69(3H, s), 3.94(2H, q, J=7.3 Hz), 4.05–4.44(3H, m), 6.98–7.02(1H, m), 7.05(1H, dd, J=2.3 Hz, 4.7 Hz), 7.07(1H, dd, J=2.3 Hz, 4.7 Hz), 7.28–7.33(1H, m)

ESI-MS(M+H)⁺: 387

EXAMPLE 11

Preparation of 1-[1-(1-methoxycarbonylpiperidin-4-yl)-piperidin-4-yl]-3-n-propyl-1,3-dihydro-2H-benzimidazol-2-one Example 1 was repeated except that the propargyl bromide was replaced with n-propyl iodide, and the title compound was obtained as a colorless oil.

¹H-NMR(CDCl₃) δ:0.97(3H, t, J=6.8 Hz), 1.46(1H, dt, J=3.9 Hz, 11.9 Hz), 1.49(1H, dt, J=3.9 Hz, 11.9 Hz), 1.79(2H, sep, J=7.2 Hz), 1.75–1.95(4H, m), 2.30–2.58(5H, m), 2.77(2H, brt, J=12.2 Hz), 3.05(2H, brd, J=6.8 Hz), 3.69 (3H, s), 3.83(2H, t, J=7.6 Hz), 4.08–4.44(3H, m), 6.96–7.10 (3H, m), 7.27–7.33(1H, m)

ESI-MS(M+H)⁺: 401

EXAMPLE 12

Preparation of 1-[1-(1-methoxycarbonylpiperidin-4-yl)-piperidin-4-yl]-3-acetyl-1,3-dihydro-2H-benzimidazol-2-one 1-[1-(1-Methoxycarbonylpiperidin -4-yl)piperidin-4-yl]-1,3-dihydro-2H-benzimidazol-2-one (32 mg) was dissolved in 5 ml of chloroform and 9 mg of acetyl chloride and 11 mg of triethylamine were added to the solution, followed by one day's stirring at room temperature. Saturated aqueous sodium bicarbonate solution was added to the reaction liquid and extracted with chloroform. The extract was dried over anhydrous sodium sulfate, concentrated, and the resulting residue was purified by silica gel column chromatography (chloroform/methanol=20/1) to provide 5.1 mg of the title compound as a colorless oil.

¹H-NMR(CDCl₃) δ:1.38–1.56(2H, m), 1.65–1.93(6H, m), 2.28–2.60 (4H, m), 2.68–2.88(1H, m), 2.75(3H, s), 3.06 (2H, brd, J=5.1 Hz), 3.70(3H,s), 4.05–4.43(3H, m), 6.95–7.38(3H, m), 8.23(1H, brd, J=7.3 Hz)

ESI-MS(M+H)⁺: 401

EXAMPLE 13

Preparation of 1-[1-(1-methoxycarbonylpiperidin-4-yl)-piperidin-4-yl]-3-(methylsulfonyl)-1,3-dihydro-2H-benzimidazol-2-one Example 12 was repeated except that the acetyl chloride was replaced with methanesulfonyl chloride, and the title compound was obtained as a pale yellow solid.

¹H-NMR(CDCl₃) δ:1.48(1H, dt, J=3.9 Hz, 12.6 Hz), 1.49 (1H, dt, J=3.9 Hz, 12.6 Hz), 1.76–1.96(4H, m), 2.26–2.58 (5H, m), 2.78(2H, brt, J=11.7 Hz), 3.05(2H, brd, J=6.9 Hz), 3.50(3H, s), 3.69(3H, s), 4.03–4.40(3H, m), 7.12 (1H, dt, J=1.7 Hz, 8.0 Hz), 7.19(1H, dt, J=1.6 Hz, 7.6 Hz), 7.31(1H, brd, J=7.9 Hz), 7.83(1H, dd, J=2.0 Hz, 7.9 Hz)

ESI-MS(M+H)⁺: 437

EXAMPLE 14

Preparation of 1-[1-(1-methoxycarbonylpiperidin-4-yl)-piperidin-4-yl]-3-(methoxycarbonyl)-1,3-dihydro-2H-benzimidazol-2-one Example 12 was repeated except that the acetyl chloride was replaced with methyl chloroformate, and the title compound. was obtained as a colorless solid.

¹H-NMR(CDCl₃) δ:1.45(1H, dt, J=3.9 Hz, 12.3 Hz)1,49 (1H, dt, J=3.9 Hz, 12.3 Hz), 1.72–1.92(4H, m), 2.32–2.61 (5H, m), 2.78(2H, brt, J=12.0 Hz), 3.05(2H, brd, J=8.1 Hz), 3.69(3H, s), 4.06(3H, s), 4.05–4.43(3H, m), 7.12 (1H, dt, J=1.5 Hz, 7.5 Hz), 7.18(1H, dt.J=1.2 Hz, 7.5 Hz), 7.24–7.31 (1H, m), 7.90–7.95(1H, m)

ESI-MS(M+H)⁺: 417

EXAMPLE 15

Preparation of 1-[1-(1-methoxycarbonylazetidin-3-yl)-piperidin-4-yl]-3-(methylsulfonyl)-1,3-dihydro-2H-benzimidazol-2-one Example 12 was repeated except that 1-[1-(1-methoxycarbonylpiperidin-4-yl) piperidin-4-yl]-1,3-dihydro-2H-benzimidazol-2-one was replaced with 1-[1-(1-methoxycarbonylazetidin-3-yl)-piperidin-4-yl]-1,3-dihydro-2H-benzimidazol-2-one which was prepared by the method of Referential Example 3, and the acetyl chloride was replaced with methanesulfonyl chloride. The title compound was obtained as a colorless oil.

¹H-NMR(CDCl₃) δ:1.55–1.93(2H, m), 1.98–2.10(2H, m), 2.39–2.58 (2H, m), 2.90–3.02(2H, m), 3.12–3.25(1H, m), 3.51(3H, s),3.68(3H, s), 3,82–3.93(2H, m), 3.97–4.09 (2H, m), 4.29–4.48(1H, m), 7.10–7.32(3H, m),7.80–7.98 (1H, m)

ESI-MS(M+H)⁺: 409

EXAMPLE 16

Preparation of 1-[1-(1-methoxycarbonylpiperidin-4-yl)-azetidin-3-yl]-3-(methylsulfonyl)-1,3-dihydro-2H-benzimidazol-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-azetidin-3-yl]-1,3-dihydro-2H-benzimidazol-2-one which was synthesized by the method of Referential Example 4 and that acetyl chloride was replaced with methanesulfonyl chloride. The title compound was obtained which was colorless and amorphous.

¹H-NMR(CDCl₃) δ:1.10–2.10(4H, m), 2.40–2.55(1H, m), 2.95–3.10 (2H, m), 3.50(3H, s), 3.70(3H, s), 3.70–3.80 (4H, m), 3.80–4.05(2H,m), 4.80–5.00(1H, m), 7.10–7.40 (2H, m), 7.48–7.55(1H, m), 7.80–7.85(1H, m)

ESI-MS(M+H)⁺: 409

EXAMPLE 17

Preparation of 1-[1-(1-methoxycarbonylpiperidin-4-yl)-piperidin-4-yl-5-methyl-3-(methylsulfonyl)-1,3-dihydro-2H-benzimidazol-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-piperidin-4-yl]-5-methyl-1,3-dihydro-2H-benzimidazol-2-one which was synthesized by the method of Referential Example 5 and that acetyl chloride was replaced with methanesulfonyl chloride. The title compound was obtained as a colorless oil.

¹H-NMR(CDCl₃) δ:1.40–1.58(2H, m), 1.77–1.91(4H, m), 2.32–2.64 (5H, m,), 2.40(3H, s), 2.50–2.75(2H, m), 3.00–3.14(2H, m), 3.48(3H, s), 3.70(3H, s), 4.11–4.39(3H, m), 6.93(1H, d, J=8.3 Hz), 7.14(1H, s), 7.67(1H, d, J=8.3 Hz)

ESI-MS(M+H)⁺: 451

EXAMPLE 18

Preparation of 1-[1-(1-methoxycarbonylpiperidin-4-yl-piperidin-4-yl]-4-fluoro-3-(methylsulfonyl)-1,3-dihydro-2H-benzimidazol-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4yl)-piperidin-4-yl]-4-fluoro-1,3-dihydro-2H-benzimidazol-2-one which was synthesized by the method of Referential Example 6 and that acetyl chloride was replaced with methanesulfonyl chloride. The title compound was obtained as a colorless oil.

¹H-NMR(CDCl₃) δ:1.20–1.90(6H, m), 2.30–2.61(5H, m), 2.70–2.84 (2H, m), 3.00–3.12(2H, m), 3.55(3H, s), 3.70(3H, s), 4.06–4.36(3H, m), 6.77–6.97(1H, m), 7.08–7.22(2H, m)

ESI-MS(M+H)⁺: 455

EXAMPLE 19

Preparation of 1-[1-(1-methoxycarbonylpiperidin-4-yl)-piperidin-4-yl]-3-(methylsulfonyl)-1,3-dihydro-2H-imidazo-[4,5-b]pyridin-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-piperidin-4-yl]-1,3-dihydro-2H-imidazo[4,5-b]pyridin-2-one which was prepared by the method of Referential Example 7 and that acetyl chloride was replaced with methanesulfonyl chloride. The title compound was obtained as a colorless solid.

¹H-NMR(CDCl₃) δ:1.35–1.58(2H, m), 1.58–1.90(4H, m), 2.27–2.45(5H, m), 2.45–2.60(1H, m), 2.60–2.85(2H, m), 2.95–3.10(2H, m), 3.53 (3H, s), 3.69(3H, s), 4.03–4.32 (2H, m), 4.30–4.48(1H, m), 7.05(1H, dd, J=5.2 Hz, 8.0 Hz), 7.94 (1H, dd, J=1.3 Hz, 8.0 Hz), 8.15(1H, dd, J=1.3 Hz, 5.2 Hz)

ESI-MS(M+H)⁺: 438

EXAMPLE 20

Preparation of 1-[1-(1-ethoxycarbonylpiperidin-4-yl)-piperidin-4-yl]-3-(methylsulfonyl)-1,3-dihydro-2H-benzimidazol-2-one 1-[1-(Piperidin-4-yl)piperidin-4-yl]-3-(methylsulfonyl)-1,3-dihydro-2H-benzimidazol-2-one.di-trifluoroacetate (28 mg) which was synthesized by the method of Referential Example 8 and 33 mg of triethylamine were dissolved in 2.5 ml of chloroform, and to which another solution of 15 mg of ethyl chloroformate in 0.2 ml of chloroform was added, followed by 8 hours stirring at room temparature. Saturated aqueous sodium hydrogencarbonate solution was added to the reaction mixture and extracted with chloroform. The extract was dried over sodium sulfate, the solvent was distilled off, and the resulting residue was purified by silica gel column chromatography (chloroform/methanol=20/1) to provide 18.4 mg of the title compound as a colorless, amorphous substance.

$^1$H-NMR(CDCl$_3$) δ:1.27(3H, t, J=7.1 Hz), 1.39–1.55(2H, m), 1.75–1.90(4H, m), 2.30–2.60(5H, m), 2.77 (2H, t-like, J=11.7 Hz), 3.00–3.10(2H, m), 3.50(3H, s), 4.13 (2H, q, J=7.1 Hz), 4.15–4.37(3H, m), 7.10–7.22(2H, m), 7.31(1H, d, J=7.7 Hz), 7.83(1H, d, J=8.0 Hz)

ESI-MS(M+H)$^+$: 451

EXAMPLE 21

Preparation of 1-[1-(1-methoxycarbonylpiperidin-4-yl)-piperidin-4-yl]-3-(methylsulfonyl)-1,3-dihydro-2H-benzimidazol-2-one Example 12 was repeated except that the acetyl chloride was replaced with ethanesulfonyl chloride. The title compound was obtained as a pale yellow solid.

$^1$H-NMR(CDCl$_3$) δ:1.36–1.56(2H, m), 1.40(3H, t, J=7.7 Hz), 1.75–1.94 (4H, m), 2.36–2.66(5H, m), 2.78(2H, brt, J=12.6 Hz), 3.08(2H, brs), 3.69 (3H, s), 3.70(2H, q, J=7.7 Hz), 4.10–4.40(3H, m), 7.12(1H, dt, J=1.4 Hz, 8.1 Hz), 7.19(1H, dt, J=1.4 Hz, 8.1 Hz), 7.28–7.38(1H, m), 7.78–7.85 (1H, m)

ESI-MS(M+H)$^+$: 451

EXAMPLE 22

Preparation of 1-[1-(1-methoxycarbonylpiperidin-4-yl)-piperidin-4-yl]-3-(n-butylsulfonyl)-1,3-dihydro-2H-benzimidazol-2-one Example 12 was repeated except that the acetyl chloride was replaced with 1-butanesulfonyl chloride. The title compound was obtained as a pale yellow solid.

$^1$H-NMR(CDCl$_3$) δ:0.92(3H, t, J=7.3 Hz), 1.34–1.58(4H, m), 1.74–1.94 (6H, m), 2.32–2.70(5H, m), 2.78(2H, brt, J=12.2 Hz), 3.04–3.20(2H, m), 3.61–3.72(2H, m), 3.70(3H, s), 4.10–4.43(3H, m), 7.07–7.15(1H, m), 7.15–7.23(1H, m), 7.30–7.40(1H, m), 7.77–7.84(1H, m)

ESI-MS(M+H)$^+$: 479

EXAMPLE 23

Preparation of 1-[1-(1-methoxycarbonylpiperidin-4-yl)-piperidin-4-yl]-3-(2,2,2-trifluoroethylsulfonyl)-1,3-dihydro-2H-benzimidazol-2-one Example 12 was repeated except that the acetyl chloride was replaced with (2,2,2-trifluoroethanesulfonyl) chloride. The title compound was obtained as a colorless oil.

$^1$H-NMR(CDCl$_3$) δ:1.45(1H, dt, J=3.9 Hz, 12.8 Hz), 1.49 (1H, dt, J=3.9 Hz, 12.8Hz), 1.74–1.92(4H, m), 2.32–2.62 (5H, m), 2.78(2H, brt, J=11.7 Hz), 3.07(2H, brd, J=8.5 Hz), 3.69(3H, s), 4.10–4.34(3H, m), 4.50(2H, q, J=8.5 Hz), 7.15(1H, dt, J=1.8 Hz, 7.9 Hz), 7.23(1H,dt, J=1.2 Hz, 7.9 Hz), 7.32 (1H, brd, J=7.9 Hz), 7.76–7.81(1H, m)

ESI-MS(M+H)$^+$: 505

EXAMPLE 24

Preparation of 1-[1-(1-methoxycarbonylpiperidin-4-yl)-piperidin-4-yl]-3-(methylsulfonyl)-5-benzimidazol-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-piperidin-4-yl]-5-fluoro-1,3-dihydro-2H-benzimidazol-2-one which was synthesized by the method of Referential Example 11 and that acetyl chloride was replaced with methanesulfonyl chloride. The title compound was obtaineda s a colorless oil.

$^1$H-NMR(CDCl$_3$) δ:1.16–1.94(8H, m), 2.22–2.61(3H, m), 2.69–2.86 (2H, m), 2.95–3.16(2H, m), 3.52(3H, s), 3.70(3H, s), 4.11–4.38(3H, s), 6.96–6.99(1H, m), 7.15–7.31 (2H, m)

ESI-MS(M+H)$^+$: 455

EXAMPLE 25

Preparation of 1-[1-(1-methoxycarbonylpiperidin-4-yl)-piperidin-4-yl]-3-(methylsulfonyl)-5-bromo-1,3-dihydro-2H-benzimidazol-2-one Example 12 was repeated except that the 1-[1-(1-methoxycarbonylpiperidin-4-yl)-piperidin-4-yl]-1,3-dihydro-2H-benzimidazol-2-one was replaced with 1-[1-(1-methoxycarbonylpiperidin-4-yl)-piperidin-4-yl]-5-bromo-1,3-dihydro-2H-benzimidazol-2-one which was synthesized by the method of Referential Example 12 and that acetyl chloride was replaced with methanesulfonyl chloride. The title compound was obtained as a colorless oil.

$^1$H-NMR(CDCl$_3$) δ:1.34–1.58(2H, m), 1.67–1.95(4H, m), 2.25–2.60(5H, m), 2.65–2.90(2H, m), 2.95–3.16(2H, m), 3.51(3H,s), 3.69(3H, s), 4.05–4.40(3H, m), 7.18(1H, d, J=8.5 Hz), 7.32(1H, dd, J=1.9 Hz,8.5 Hz), 7.98(1H, d, J=1.9 Hz)

ESI-MS(M+H)$^+$: 515($^{79}$Br isotope)

EXAMPLE 26

Preparation of 1-[1-(1-methoxycarbonylpiperidin-4-yl)-piperidin-4-yl]-3-(methylsulfonyl)-6-fluoro-1,3-dihydro-2H-benzimidazol-2-one Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-piperidin-4-yl]-6-fluoro-1,3-dihydro-2H-imidazol-2-one which was synthesized by the method of Referential Example 13 and that acetyl chloride was replaced with methanesulfonyl chloride. The title compound was obtained as a colorless oil.

$^1$H-NMR(CDCl$_3$) δ:1.46(2H, dq, J=4.3 Hz, 12.1 Hz), 1.66–1.92(4H, m), 2.38–2.60(5H, m), 2.77(2H, brt, J=12.1 Hz), 2.98–3.13(2H, m), 3.50(3H, s), 3.69(3H, s), 4.10–4.35 (3H, m), 6.83(1H, dt, J=2.7 Hz, 8.9 Hz), 7.07(1H, dd, J=2.7 Hz, 8.9 Hz), 7.74(1H, dd, J=4.4 Hz, 8.9 Hz)

ESI-MS(M+H)$^+$: 455

EXAMPLE 27

Preparation of 1-[1-(1-methoxycarbonylpiperidin-4-yl)-piperidin-4-yl]-3-(methylsulfonyl)-6-hydroxy-1,3-dihydro-2H-benzimidazol-2-one.monohydrochloride Example 12 was repeated except that the 1-[1-(1-methoxycarbonylpiperidin-4-yl)piperidin-4-yl]-1,3-dihydro-2H-benzimidazol-2-one was replaced with 1-[1-(1-methoxycarbonylpiperidin-4-yl)-piperidin-4-yl]-6-methoxymethyloxy-1,3-dihydro-2H-benzimidazol-2-one which was synthesized by the method of Referential Example 14 and that acetyl chloride was replaced with methanesulfonyl chloride. Thereafter the product was dissolved in 10% hydrochloric acid-methanol and stirred for 12 hours at room temperature. Then distilling the solvent off, the title compound was obtained as a pale yellow solid.

$^1$H-NMR(D$_2$O) δ:1.55–1.83(2H, m), 2.07–2.27(4H, m), 2.60–2.98 (4H, m), 3.15–3.80(5H, m), 3.46(3H, s), 3.66(3H, s), 4.17–5.05(3H, m), 6.69(1H, dd, J=2.2 Hz, 8.9 Hz), 6.82 (1H, d, J=2.2 Hz), 7.52(1H, d, J=8.9 Hz)

ESI-MS(M+H)$^+$: 453

EXAMPLE 28

Preparation of 1-[1-(1-methoxycarbonylpiperidin-4-yl)-piperidin-4-yl]-3-(methylsulfonyl)-5-hydroxy-1,3-dihydro-2H-benzimidazol-2-one.monohydrochloride After conducting the reaction as described in Example 12 using 1-[1-(1-methoxycarbonylpiperidin-4-yl)-piperidin-4-yl]-5-methoxymethyloxy-1,3-dihydro-2H-benzimidazol-2-one instead of 1-[1-(1-methoxycarbonylpiperidin-4-yl) piperidin-4-yl]-1,3-dihydro-2H -benzimidazol-2-one, and methanesulfonyl chloride instead of acetyl chloride, the product was dissolved in 10% hydrochloric acid-methanol and stirred for 12 hours at room temperature. Then distilling the solvent off, the title compound was obtained as a pale yellow solid.

$^1$H-NMR(CD$_3$OD) δ:1.55–1.85(2H, m), 2.08–2.23(4H, m), 2.69–3.81 (9H, m), 3.50(3H, s), 3.70(3H, s), 4.20–4.99 (3H, m), 6.70(1H, dd, J=2.5 Hz, 8.7 Hz), 7.10–7.36(1H, m), 7.30 (1H, d, J=2.5 Hz)

ESI-MS(M+H)$^+$: 453

EXAMPLE 29

Preparation of 1-[1-(1-methoxycarbonylpiperidin-4-yl)-piperidin-4-yl]-3-carbamoyl-1,3-dihydro-2H-benzimidazol-2-one 1-[1-(1-Methoxycarbonylpiperidin-4-yl)piperidin-4-yl]-1,3-dihydro-2H-benzimidazol-2-one (49 mg) and 30 mg of triethylamine were dissolved in 4 ml of chloroform, and to which 30 mg of (4-nitrophenyl) chloroformate was added, followed by 30 minutes' stirring at room temperature. Thereafter the solvent was distilled off, and the resulting residue was dissolved in 5 ml of tetrahydrofuran. To the solution 1 ml of aqueous ammonia was added and stirred for 30 minutes at room temperature. Then water was added to the reaction liquid, followed by extraction with ethyl acetate. The organic layer was washed with saturated brine, dried over anhydrous magnesium sulfate, concentrated and the resulting residue was purified by silica gel column chromatography (chloroform/methanol=20/1) to provide 38 mg of the title compound as a colorless solid.

$^1$H-NMR(CDCl$_3$) δ:1.38–1.58(2H, m), 1.62–2.00(4H, m), 2.31–2.64 (5H, m), 2.70–2.91(2H, m), 3.00–3.20(2H, m), 3.70(3H, s), 4.04–4.42 (3H, m), 5.28–5.50(1H, m), 7.11–7.40(3H, m), 8.18–8.30(1H, m), 8.60–8.76 (1H,m)

ESI-MS(M+H)$^{30}$: 402

EXAMPLE 30

Preparation of 1-[1-(1-methoxycarbonylpiperidin-4-yl)-piperidin-4-yl]-3-(isopropylsulfonyl)-1,3-dihydro-2H-benzimidazol-2-one Example 1 was repeated except that the propargyl bromide was replaced with (isopropylsulfonyl) chloride, and the title compound was obtained as a colorless oil.

$^1$-NMR(CDCl$_3$) δ:1.45(1H, dt, J=4.4 Hz, 11.9 Hz), 1.49 (1H, dt, J=4.4 Hz, 11.9 Hz), 1.73–1.98(4H, m), 2.30–2.59 (5H, m), 2.77(2H, brt, J=11.9 Hz), 3.05(2H, brd, J=7.6 Hz), 3.69(3H, s), 3.76(3H, s), 4.08–4.44(3H, m), 4.63(2H,s), 6.84–6.92(1H, m), 7.02–7.11(2H, m), 7.26–7.29(1H, m)

ESI-MS(M+H)$^+$: 431

EXAMPLE 31

Preparation-of 1-[1-(1-methoxycarbonylpiperidin-4-yl)-piperidin-4-yl]-3-(3,3,3-trifluoropropyl)-1,3-dihydro-2H-benzimidazol-2-one Example 1 was repeated except that the propargyl bromide was replaced with 3-bromo-1,1,1-trifluoropropane, and the title compound was obtained as a colorless oil.

$^1$H-NMR(CDCl$_3$) δ:1.38–1.56(2H, m), 1.76–1.91(4H, m), 2.28–2.68 (7H, m), 2.77(2H, brt, J=11.4 Hz), 3.05 (2H, brd, J=6.7 Hz), 3.69(3H, s), 4.02–4.48(5H, m), 6.95–7.01 (1H, m), 7.02–7.13(2H, m), 7.28–7.34(1H, m)

ESI-MS(M+H)$^+$: 455

EXAMPLE 32

Preparation of 1-[1-(1-methoxycarbonylpiperidin-4-yl)-piperidin-4-yl]-3-(2-fluoroethyl)-1,3-dihydro-2H-benzimidazol-2-one Example 1 was repeated except that the propargyl bromide was replaced with 1-bromo-2-fluoroethane, and the title compound was obtained as an orange-tinted oil.

$^1$H-NMR(CDCl$_3$) δ:1.47(2H, dq, J=3.9 Hz, 12.3 Hz), 1.74–1.94(4H, m), 2.24–2.58(5H, m), 2.77(2H, brt, J=12.3 Hz), 3.05(2H, brd, J=7.9 Hz), 3.69(3H, s), 4.06–4.42(3H, m), 4.17(2H, dt, J=26.1 Hz, 4.9 Hz), 4.71(2H, dt, J=47.1 Hz, 4.9 Hz), 7.01–7.13(3H, m), 7.26–7.33(1H, m)

ESI-MS(M+H)$^+$: 405

EXAMPLE 33

Preparation of 1-[1-(1-methoxycarbonylpiperidin-4-yl)-piperidin-4-yl]-3-(2,2-difluoroethyl)-1,3-dihydro-2H-benzimidazol-2-one Example 1 was repeated except that the propargyl bromide was replaced with 2-bromo-1,1-difluoroethane, and the title compound was obtained as an orange-tinted oil.

$^1$-NMR(CDCl$_3$) δ:1.47(2H, dq, J=3.9 Hz, 11.8 Hz), 1.74–1.92(4H, m), 2.32–2.58(5H, m), 2.78(2H, brt, J=12.2 Hz), 2.98–3.10(2H, m), 3.69(3H, s), 4.10–4.42(3H, m), 4.21 (2H, dt, J=4.3 Hz, 13.8 Hz), 6.04(1H, tt, J=4.3 Hz, 55.8 Hz), 7.02–7.13(3H, m), 7.25–7.34(1H, m)

ESI-MS(M+H)$^+$: 423

EXAMPLE 34

Preparation of 1-[1-(1-methoxycarbonylpiperidin-4-yl)-piperidin-4-yl]-3-prenyl-1,3-dihydro-2H-benzimidazol-2-one Example 1 was repeated except that the propargyl bromide was replaced with prenyl bromide, and the title compound was obtained as a colorless oil.

$^1$H-NMR(CDCl$_3$) δ:1.30–1.60(2H, m), 1.72(3H, s), 1.75–1.95(8H, m), 2.25–2.60(4H, m), 2.70–2.85(2H, t-like), 2.95–3.10(2H, m), 3.69(3H, s), 4.10–4.50(3H, m), 4.47 (2H, d, J=6.6 Hz), 5.20–5.30(1H, m), 6.90–7.10(3H, m), 7.20–7.35(1H, m)

ESI-MS(M+H)$^+$: 427

EXAMPLE 35

Preparation of 1-[1-(1-methoxycarbonylpiperidin-4-yl)-piperidin-4-yl]-3-(2-ethoxyethyl)-1,3-dihydro-2H-benzimidazol-2-one Example 1 was repeated except that the propargyl bromide was replaced with ethyl (2-bromoethyl) ether, and the title compound was obtained as a colorless oil.

$^1$H-NMR(CDCl$_3$) δ:1.15(3H, t, J=6.8 Hz), 1.47(2H, dq, J=3.9 Hz, 11.8 Hz), 1.74–1.90(4H, m), 2.30–2.58(5H, m), 2.77 (2H, brt,J=11.8 Hz), 2.98–3.08 (2H, m), 3.48(2H, q, J=6.8 Hz), 3.69(3H, s), 3.70(2H, t, J=6.1 Hz), 4.05 (2H, t, J=6.1 Hz), 4.10–4.42(3H, m), 6.99–7.17(3H, m), 7.25–7.31 (1H, m)

ESI-MS(M+H)$^+$: 431

EXAMPLE 36

Preparation of 1-[1-(1-methoxycarbonylpiperidin-4-yl)-piperidin-4-yl]-3-(ethoxycarbonylmethyl)-1,3-dihydro-2H-benzimidazol-2-one Example 1 was repeated except that the propargyl bromide was replaced with ethyl bromoacetate, and the title compound was obtained as a colorless oil.

$^1$H-NMR(CDCl$_3$) δ:1.26(3H, t, J=7.4 Hz), 1.38–1.55(2H, m), 1.74–1.92(4H, m), 2.32–2.58(5H, m), 2.78(2H, brt, J=11.7 Hz), 3.06(2H, brd, J=7.1 Hz), 3.69(3H, s), 4.12–4.42 (3H, m), 4.22(2H, q, J=7.4 Hz), 4.61(2H, s), 6.84–6.92(1H, m), 7.02–7.11(2H, m),7.27–7.34(1H, m)

ESI-MS(M+H)$^+$: 445

EXAMPLE 37

Preparation of 1-[1-(1-methoxycarbonylpiperidin-4-yl)-piperidin-4-yl]-3-(2-oxo-n-butyl)-1,3-dihydro-2H-benzimidazol-2-one Example 1 was repeated except that the propargyl bromide was replaced with 1-(methylsulfonyloxy)-2-butanone, and the title compound was obtained as a colorless oil.

$^1$H-NMR(CDCl$_3$) δ:1.09(3H, t, J=7.3 Hz), 1.45(1H, dt, J=3.5 Hz,11.5 Hz), 1.49(1H, dt, J=3.5 Hz, 11.5 Hz), 1.76–1.92 (4H, m), 2.32–2.58(5H, m), 2.50 (2H, q, J=7.3 Hz), 2.78 (2H, brt, J=12.2 Hz), 3.05(2H, brd, J=8.0 Hz), 3.69(3H, s), 4.10–4.42(3H, m), 4,61(2H,s), 6.74–6.82(1H, m), 7.00–7.11(2H, m), 7.28–7.34(1H, m)

ESI-MS(M+H)$^+$: 429

EXAMPLE 38

Preparation of 1-[1-(1-ethoxycarbonylpiperidin-4-yl)-piperidin-4-yl]-3-methyl-1,3-dihydro-2H-benzimidazol-2-one Example 1 was repeated except that the propargyl bromide was replaced with methyl iodide and 1-[1-(1-methoxycarbonylpiperidin-4-yl)-piperidin-4-yl]-1,3-dihydro-2H-benzimidazol-2-one was replaced with 1-[1-(1-ethoxycarbonylpiperidin-4-yl-piperidin-4-yl]-1,3-dihydro-2H-benzimidazol-2-one which was synthesized by the method of Referential Example 16, and the title compound was obtained as a colorless oil.

$^1$H-NMR(CDCl$_3$) δ:1.26(3H, t, J=7.2 Hz), 1.40–1.60(2H, m), 1.70–1.90 (4H, m), 2.30–2.60(5H, m), 2.70–2.85(2H, m), 2.98–3.10(2H, m), 3.41(3H, s), 4.13(2H, q, J=7.2 Hz), 4.10–4.45(3H, m), 6.90–7.15(3H, m), 7.20–7.31(1H, m)

ESI-MS(M+H)$^+$: 387

EXAMPLE 39

Preparation of 1-[1-(1-methoxycarbonylpiperidin-4-yl)-piperidin-4-yl]-3-(2-hydroxyethyl)-1,3-dihydro-2H-benzimidazol-2-one Three-hundred (300) mg of 1-[1-(1-methoxycarbonylpiperidin-4-yl)piperidin-4-yl]-1,3-dihydro-2H-benzimidazol-2-one was dissolved in 15 ml of tetrahydrofuran, and to which 33 mg of 60% sodium hydride was added. After evolution of a gas ceased, 93 μl of (2-bromoethyl)acetate was added, heated to 40° C. and stirred for 2 hours. The reaction liquid was concentrated and the remaining matter was distributed between water and chloroform. The chloroform layer was separated, dried over anhydrous sodium sulfate, concentrated and the residue was purified by silica gel column chromatography (chloroform/methanol=19/1). Thus 354 mg of 1-[1-(1-methoxycarbonylpiperidin-4-yl)-piperidin-4-yl]-3-(2-acetoxy-ethyl)-1,3-dihydro-2H-benzimidazol-2-one was obtained. The product was dissolved in 10 ml of methanol, to which 35 mg of sodium borohydride was added and stirred for 7 hours at room temperature. The reaction liquid was concentrated, to which water was added and extracted with chloroform. The chloroform layer was dried over anhydrous sodium sulfate and then concentrated. The residue was purified by silica gel column chromatography (chloroform/methanol=19/1), to provide 246 mg of the title compound as a colorless, amorphous substance.

$^1$H-NMR(CDCl$_3$) δ:1.46(2H, dq, J=4.4 Hz, 12.3 Hz), 1.82 (4H, brd, J=9.4 Hz), 2.30–2.58(5H, m),2.77(2H, brd, J=11.9 Hz), 3.03(2H, brd, J=8.0 Hz), 3.28(1H, brs), 3.69(3H, s), 3.95 (2H, t, J=4.9 Hz), 4.04(2H, t, J=4.9 Hz), 4.12–4.42(3H, m), 7.01–7.12(3H, m), 7.27–7.34(1H, m)

ESI-MS(M+H)$^+$: 403

EXAMPLE 40

Preparation of 1-[1-(1-methoxycarbonylpiperidin-4-yl)-piperidin-4-yl]-3-(methylthiomethyl)-1,3-dihydro-2H-benzimidazol-2-one Example 1 was repeated except that the propargyl bromide was replaced with (chloromethyl)methyl sulfide, and the title compound was obtained as a red-tinted oil.

$^1$H-NMR(CDCl$_3$) δ:1.47(2H, dq, J=4.3 Hz, 12.5 Hz), 1.74–1.90(4H, m), 2.16(3H, s), 2.32–2.58(5H, m), 2.78 (2H, brt, J=12.5 Hz), 2.96–3.12(2H, m), 3.69(3H, s), 4.10–4.44 (3H, m), 4.98(2H, s), 7.06–7.15(3H, m), 7.25–7.33 (1H, m)

ESI-MS(M+H)$^+$: 419

EXAMPLE 41

Preparation of 1-[1-(1-methoxycarbonylpiperidin-4-yl)-piperidin-4-yl]-3-(methylsulfonylmethyl)-1,3-dihydro-2H-benzimidazol-2-one 1-[1-(1-Methoxycarbonylpiperidin-4-yl)-piperidin-4-yl]-3-methylthiomethyl)-1,3-dihydro-2H-benzimidazol-2-one (390 mg) was dissolved in 10 ml of dichloromethane, and to which 345 mg of m-chloroperbenzoic acid was added, followed by an hour's heating under reflux. After cooling the reaction liquid, saturated aqueous sodium hydrogencarbonate solution was added to the reaction liquid and extracted with chloroform. The chloroform layer was washed with saturated aqueous sodium hydrogencarbonate solution, dried over anhydrous sodium sulfate, and the solvent was distilled off. The residue was purified by silica gel column chromatography (chloroform/methanol=20/1) to provide 100 mg of the title compound as a colorless oil.

$^1$H-NMR(CDCl$_3$) δ:1.38–1.56(2H, m), 1.76–1.98(4H, m), 2.32–2.60 (5H, m), 2.78(2H, brt, J=12.9 Hz), 2.98(3H, s), 3.02–3.10(2H, m), 3.69(3H, s), 3.80–3.96(1H, m), 4.12–4.38(2H, m), 5.06(2H, s), 7.11–7.19(2H, m), 7.25–7.35(2H, m)

ESI-MS(M+H)$^+$: 451

EXAMPLE 42

Preparation of 1-[1-(1-methoxycarbonylpiperidin-4-yl)-piperidin-4-yl]-3-(2-methylsulfonylethyl)-1,3-dihydro-2H-benzimidazol-2-one Example 1 was repeated except that the propargyl bromide was replaced with methanesulfonic acid 2-(methylsulfonyl)ethyl ester, and the title compound was obtained as a colorless oil.

$^1$H-NMR(CDCl$_3$) δ:1.47(2H, dq, J=4.2 Hz, 12.3 Hz), 1.74–1.90(4H, m), 2.30–2.58(5H, m), 2.78(2H, brt, J=12.3 Hz), 2.91(3H, s), 3.05(2H, brd, J=6.8 Hz), 3.48(2H, t, J=6.8 Hz), 3.69(3H, s), 4.10–4.40(3H, m), 4.36 (2H, t, J=6.8 Hz), 7.05–7.18(3H, m), 7.25–7.35(1H, m)

ESI-MS(M+H)$^+$: 465

EXAMPLE 43

Preparation of 1-[1-(1-methoxycarbonylpiperidin-4-yl)-piperidin-4-yl]-3-(2-methylthioethyl)-1,3-dihydro-2H-benzimidazol-2-one Example 1 was repeated except that the propargyl bromide was replaced with methanesulfonic acid 2-(methylthio)ethyl ester, and the title compound was obtained as a colorless oil.

$^1$H-NMR(CDCl$_3$) δ:1.47(2H, dq, J=3.9 Hz, 12.2 Hz), 1.74–1.90(4H, m), 2.18(3H, s), 2.30–2.58(5H, m), 2.77 (2H, brt, J=12.2 Hz), 2.84 (2H, t, J=7.2 Hz), 3.04(2H, brd, J=6.6 Hz), 3.69(3H, s), 4.08(2H, t, J=7.2 Hz), 4.13–4.42(3H, m), 6.95–7.17(3H, m), 7.20–7.40(1H, m)

ESI-MS(M+H)$^+$: 433

EXAMPLE 44

Preparation of 1-[1-(1-ethoxycarbonylpiperidin-4-yl)-piperidin-4-yl]-3-(ethoxycarbonyl)-1,3-dihydro-2H-benzimidazol-2-one 1-[1-(Piperidin-4-yl)piperidin-4-yl]-1,3-dihydro-2H-benzimidazol-2-one-dihydrochloride (37.3 mg) was dissolved in 3 ml of chloroform, and to which 21 μl of ethyl chloroformate and 84 μl of triethylamine were successively added under cooling with ice, followed by overnight stirring at room temperature. To the reaction liquid saturated aqueous sodium hydrogencarbonate solution was added and extracted with chloroform. The organic layer was washed with saturated. brine, dried over anhydrous sodium sulfate and then the solvent was distilled off. The resulting residue was purified by silica gel column chromatography (chloroform/methanol=10/1) to provide 41.7 mg of the title compound as a colorless oil.

$^1$H-NMR(CDCl$_3$) δ:1.26(3H, t, J=6.9 Hz), 1.48 (3H, t, J=7.2 Hz), 1.35–1.55 (1H, m), 1.65–1.90(5H, m), 2.30–2.60 (5H, m), 2.67–2.85(2H, m), 2.98–3.10(2H, m), 4.13(2H, q, J=6.9 Hz), 4.05–4.45(3H, m), 4.52(2H, q, J=7.2 Hz), 7.05–7.30(3H, m), 7.90–7.95(1H, m)

ESI-MS(M+H)$^+$: 445

Referential Example 1

Preparation of 1-[1-(1-methoxycarbonylpiperidin-4-yl)-piperidin-4-yl]-1,3-dihydro-2H-benzimidazol-2-one Fourty-one (41) mg of 1-[1-(piperidin-4-yl)piperidin-4-yl]-1,3-dihydro-2H-benzimidazol-2-one di-trifluoroacetate was dissolved in 5 ml of chloroform, and to which 25 mg of diisopropylethylamine and 9.4 mg of methyl chloroformate were added, followed by stirring overnight. The reaction mixture was distributed between chloroform and saturated aqueous sodium bicarbonate solution, and the organic layer was dried over sodium sulfate and concentrated. The resulting residue was purified by silica gel column chromatography (chloroform/methanol=10/1) to provide 18 mg of the title compound as a colorless, amorphous substance.

Referential Example 2

Preparation of 1-(methylsulfonyloxy)acetone

Thirty-seven (37) mg of hydroxyacetone was dissolved in 2 ml of chloroform, and to which 0.078 ml of methanesulfonyl chloride was added. After stirring the reaction liquid at room temperature for 30 minutes, saturated aqueous sodium bicarbonate solution was added and extracted with chloroform. The extract was dried over anhydrous sodium sulfate and concentrated to provide the title compound.

Referential Example 3

Preparation of 1-[1-(1-methoxycarbonylazetidin-3-yl)-piperidin-4-yl]-1,3-dihydro-2H-benzimidazol-2-one In 7 ml of methanol, 217 mg of 1-(piperidin-4-yl)-1,3-dihydro-2H-benzimidazol-2-one, 300 mg of 1-(diphenylmethyl)azetidin-2-one, 94 mg of sodium cyanoborohydride and 102 mg of zinc chloride were dissolved and stirred overnight. The reaction liquid was added to a saturated aqueous solution of sodium hydrogencarbonate to which sodium chloride had been added, and extracted with ethyl acetate. The extract was washed with saturated brine, dried over sodium sulfate and concentrated. Thus obtained residue was purified by silica gel column chromatography (chloroform, chloroform/methanol=50/1) to provide 583 mg of crude 1-[1-[1-(diphenylmethyl)azetidin-3-yl]piperidin-4-yl]-1,3-dihydro-2H-benzimidazol-2-one.

From said crude product 500 mg was taken and dissolved in 10 ml of methanol, to which 2 ml of 10% hydrogen chloride/methanol was added, and hydrogenation was conducted on 150 mg of palladium hydroxide/carbon, in hydrogen atmosphere of 3 atmospheres. The reaction liquid was filtered, the filtrate was rendered alkaline with 1N-aqueous sodium hydroxide solution, and extracted with chloroform. The extract was dried over sodium sulfate, concentrated, and the residue obtained was purified by silica gel column chromatography (chloroform, chloroform/methanol=20/1) to provide 168 mg of 1-[1-(azetidin-3-yl)piperidin-4-yl]-1,3-dihydro-2H-benzimidazol-2-one.

Eighty (80) mg of said product was dissolved in 3 ml of chloroform, 30 mg of methyl chlorofomate and 60 mg of diisopropylethylamine were added, stirred for 2 hours, and concentrated. The residue was distributed between 1N aqueous sodium hydroxide solution and chloroform, and the organic layer was dried over sodium sulfate and concen-

Referential Example 4

Preparation of 1-[1-(1-methoxycarbonylpiperidin-4-yl)-azetidin-3-yl]-1,3-dihydro-2H-benzimidazol-2-one In 15 ml, 0.46 ml of o-nitrofluorobenzene, 1.05 g of 3-amino-1-diphenylmethylazetidine and 1.1 g of potassium carbonate were suspended, which suspension was stirred at room temperature for 17 hours. The reaction solution was poured into water, diluted with ethyl acetate, washed with water three times, further washed with saturated brine and dried over anhydrous sodium sulfate. Distilling the solvent off, 1.6 g of an orange-colored residue was obtained.

To the product 1.65 g of stannic chloride was added and together dissolved in 20 ml of dimethylformamide, followed by 3 hours' stirring at room temperature. Further 1.65 g of stannic chloride was added and stirred overnight. The reaction solution was poured into 4N aqueous sodium hydroxide solution to render the system alkaline, followed by extraction with chloroform. Further the organic layer was washed with water and then with saturated brine, dried over anhydrous sodium sulfate and the solvent was distilled off, leaving 10.6 g of black residue. Onto the residue 0.71 g of carbodiimidazole was added, followed by stirring overnight at room temperature. The reaction solution was poured into saturated aqueous sodium hydrogencabonate solution and extracted with ethyl acetate. The organic layer was washed with saturated brine and dried over anhydrous sodium sulfate. Distilling the solvent off, 1.59 g of black residue was obtained, which was purified by silica gel column chromatography (chloroform/methanol=200/1), to provide 630 mg of 1-[1-(diphenylmethyl)azetidin-3-yl]-1,3-dihydro-2H-benzimidazol-2-one.

Said product was dissolved in methanol, 1N-aqueous hydrochloric acid and 60 mg of palladium hydroxide/carbon were added, and shaken overnight in hydrogen atmosphere of 4 atmospheres. Filtering the catalyst off and distilling off the methanol in the filtrate, 484 mg of black residue was obtained. Thirty (30) mg of the product was dissolved in 2 ml of chloroform, to which 36 mg of 1-(methoxycarbonyl) piperidone was added, followed by an hour's stirring at room temperature. Further 42 mg of sodium triacetoxyborohydride was added, followed by stirring overnight. The reaction solution was poured into saturated aqueous sodium hydrogencarbonate solution and extracted with chloroform three times. The extract was washed with saturated brine, dried over anhydrous sodium sulfate, and the solvent was distilled off to provide an yellow residue. The residue was purified by silica gel column chromatography (chloroform/methanol=10/1), to provide 6.1 mg of the title compound.

Referential Example 5

Preparation of 1-[1-(1-methoxycarbonylpiperidin-4-yl)-piperidin-4-yl]-5-methyl-1,3-dihydro-2H-benzimidazol-2-one In 20 ml of ethanol, 1.55 g of 4-fluoro-3-nitrotoluene, 1.90 g of 4-amino-1-benzylpiperidine and 1.40 g of potassium carbonate were suspended, and refluxed under heating for 30 minutes. Ethyl acetate and brine were added to the reaction liquid, mixed by shaking and the organic layer was separated. The organic layer was dried over sodium sulfate and concentrated to give 3.6 g of an orange-colored oil, 500 mg of which was dissolved in 5 ml of methanol. The solution was stirred for 2 hours in hydrogen atmosphere, on 50 mg of palladium/carbon. The reaction liquid was filtered, concentrated, dissolved in 15 ml of chloroform and to which 300 mg of carbonyldiimidazole was added, followed by 30 minutes' stirring. The reaction liquid was concentrated, and the resulting residue was purified by silica gel column chromatography (chloroform, chloroform/methanol=100/1) to provide 147 mg of 1-(1-benzylpiperidin-4-yl)-5-methyl-1,3-dihydro-2H-benzimidazol-2-one. The product was dissolved in methanol, and into which a catalytic amount of palladium hydroxide/carbon was added, followed by 0.5 hour's stirring in hydrogen atmosphere. The reaction liquid was filtered and concentrated to give 95.8 mg of 1-(piperidin-4-yl)-5-methyl-1,3-dihydro-2H-benzimidazol-2-one as a gray oil. Seventy (70) mg of the oil was taken into 6 ml of methanol, and into which 300 mg of 1-(methoxycarbonyl)piperidone, 170 mg of sodium cyanoborohydride and 184 mg of zinc chloride were added, followed by overnight stirring at room temperature. To the reaction liquid, ethyl acetate and saturated aqueous sodium hydrogencarbonate solution to which sodium chloride had been added were added, shaken and separated. The organic layer was dried over sodium sulfate, concentrated, and the resulting residue was purified by silica gel column chromatography (chloroform, chloroform/methanol=50/1) to provide 71.6 mg of the title compound.

Referential Example 6

Preparation of 1-[1-(1-methoxycarbonylpiperidin-4-yl)-piperidin-4-yl]-4-fluoro-1,3-dihydro-2H-benzimidazol-2-one Using 2,6-difluoro-1-nitrobenzene as the starting material, the title compound was obtained following the procedures of Referential Examples 9 and 10.

Referential Example 7

Preparation of 1-[1-(1-methoxycarbonylpiperidin-4-yl)-piperidin-4-yl]-1,3-dihydro-2H-imidazo[4,5-b]-pyridin-2-one Seventy (70) mg of 2-chloro-3-nitropyridine, 140 mg of sodium hydrogencarbonate, 35 mg of potassium iodide and 137 mg of 4-(4-aminopiperidin-1-yl)-1-(methoxycarbonyl) piperidine were stirred in 5 ml of cyclohexanol at 150° C. for 4 hours. After cooling, the reaction liquid was extracted with ethyl acetate and the extract was washed with saturated brine, dried over anhydrous sodium sulfate and concentrated. Thus obtained crude product was purified by silica gel column chromatography (chloroform/methanol=95/5) to provide 76 mg of 2-[1-(1-methoxycarbonylpiperidin-4-yl)-piperidin-4-yl]-amino-3-nitropyridine.

Seventy (70) mg of 2-[1-(1-methoxycarbonylpiperidin-4-yl)-piperidin-4-yl]amino-3-nitropyridine was dissolved in 5 ml of methanol, and to which 20 mg of 10% palladium/carbon catalyst was added to effect catalytic reduction at room temperature under atmospheric pressure of hydrogen. After filtering the catalyst off and drying the filtrate to solid, the resulting residue was purified by silica gel column chromatography (chloroform/methanol=95/5) to give 20 mg of 3-amino-2-[1-(1-methoxycarbonylpiperidin-4-yl)-piperidin-4-yl]aminopyridin.

Twenty (20) mg of 3-amino-2-[1-(1-methoxycarbonylpiperidin-4-yl)piperidin-4-yl]aminopyridin and 18 mg of triphosgene were dissolved in 2 ml of tetrahydrofuran, and to which 45 μl of triethylamine was added under cooling with ice. The system was further stirred at the same temperature for 2 hours and for an hour, at room temperature. Thereafter water was added to the reaction liquid and extracted with chloroform. The extract was dried over anhydrous sodium sulfate, concentrated and the resulting crude product was purified by silica gel chromatography (chloroform/methanol=10/1) to give 12 mg of the title compound.

Referential Example 8

Preparation of 1-[1-(piperidin-4-yl)piperidin-4-yl]-3-(methylsulfonyl)-1,3-dihydro-2H-benzimidazol-2-one.di-trifluoroacetate One (1) g of 1-[1-(1-(tert-butoxycarbonyl)piperidin-4-yl)-piperidin-4-yl]-1,3-dihydro-2H-benzimidazol-2-one (cf. International Publication WO 96/13262) and 0.53 ml of triethylamine were suspended in 30 ml of chloroform. To the suspension 0.29 ml of methanesulfonyl chloride was added, followed by 2 hours' stirring at room temperature. Saturated aqueous sodium hydrogencarbonate solution was added to the reaction liquid, which was then extracted with chloroform. The extract was dried over sodium sulfate, concentrated, and the resulting residue was purified by silica gel column chromatography (chloroform, chloroform/methanol=19/1) to give 860 mg of 1-[1-(1-(tert-butoxycarbonyl)piperidin-4-yl)piperidin-4-yl]-3-(methylsulfonyl)-1,3-dihydro-2H-benzimidazol-2-one. The product was dissolved in 25 ml of trifluoroacetic acid, stirred for 30 minutes at room temperature and then the trifluoroacetic acid was distilled off. To the residue ether and chloroform were added and whereby obtained crystals were recovered by filtration, to give 860 mg of the title compound.

Referential Example 9

Preparation of methyl 4-{4-(4-methylsulfonyl-2-aminophenyl)-amino]piperidin-1-yl}piperidine-1-carboxylate In 5 ml of ethanol, 125 mg of 4-(4-aminopiperidin-1-yl)-1-(methoxycarbonyl)piperidine, 115 mg of 1-fluoro-4-(methylsulfonyl)-2-nitrobenzene and 88 mg of potassium carbonate were suspended, and heated to 75° C. for 2 hours. The reaction liquid was cooled, and to which ethyl acetate and saturated brine were added and mixed by shaking. The organic layer was washed with saturated brine, dried over sodium sulfate and concentrated. The resulting residue was purified by silica gel column chromatography (chloroform, chloroform/methanol=50/1), to give 207 mg of methyl 4-{4-(4-methyl-sulfonyl-2-nitrophenyl)amino]piperidin-1-yl}piperidine-1-carboxylate. Eighty-eight (88) mg of said product was taken into 5 ml of 1N hydrochloric acid, and 500 mg of iron was added thereto, followed by 2 hours' stirring. The reaction liquid was neutralized by addition of saturated aqueous sodium hydrogencarbonate solution and extracted with ethyl acetate. The extract was washed with saturated brine, dried over sodium sulfate and concentrated to give 80 mg of the title compound.

Referential Example 10

Preparation of 1-[1-(1-methoxycarbonylpiperidin-4-yl)-piperidin-4-yl]-5-(methylsulfonyl)-1,3-dihydro-2H-benzimidazol-2-one Eighty (80) mg of methyl 4-{4-(4-methylsulfonyl-2-aminophenyl)amino]piperidin-1-yl}piperidine-1-carboxylate which was synthesized by the method of Referential Example 9 was dissolved in ethyl acetate, and to which 150 mg of carbonyl-di-imidazole was added, followed by 3 hours' stirring at room temperature. The reaction liquid was concentrated, and the resulting residue was purified by silica gel column chromatography (chloroform, chloroform/methanol=40/1) to give 79 mg of the title compound as colorless oil.

Referential Example 11

Preparation of 1-[1-(1-methoxycarbonylpiperidin-4-yl)-piperidin-4-yl]-5-fluoro-1,3-dihydro-2H-benzimidazol-2-one Using 1,4-difluoro-2-nitrobenzene as the starting material, the title compound was obtained following the procedures of Referential Examples 9 and 10.

Referential Example 12

Preparation of 1-[1-(1-methoxycarbonylpiperidin-4-yl)-piperidin-4-yl]-5-bromo-1,3-dihydro-2H-benzimidazol-2-one Using 1-fluoro-2-nitro-4-bromobenzene as the starting material, the title compound was obtained following the procedures of Referential Examples 9 and 10.

Referential Example 13

Preparation of 1-[1-(1-methoxycarbonylpiperidin-4-yl)-piperidin-4-yl]-6-fluoro-1,3-dihydro-2H-benzimidazol-2-one Using 1-nitro-2,4-difluorobenzene as the starting material, the title compound was obtained following the procedures of Referential Examples 9 and 10.

Referential Example 14

Preparation of 1-[1-(1-methoxycarbonylpiperidin-4-yl)piperidin-4-yl]-6-methoxymethyloxy-1,3-dihydro-2H-benzimidazol-2-one Three-hundred (300) mg of 2-nitro-5-hydroxy-1-fluorobenzene was dissolved in chloroform, and to which 0.17 ml of chloromethyl methyl ether and 0.48 ml of diisopropylethylamine were added, followed by 30 minutes' stirring at 0° C. The reaction liquid was diluted with ethyl acetate, washed with water and saturated brine, and dried over anhydrous sodium sulfate. The solvent was concentrated and the residue was reacted following the procedures of Referential Examples 9 and 10, to provide the title compound.

Referential Example 15

Preparation of 1-[1-(1-methoxycarbonylpiperidin-4-yl)-piperidin-4-yl]-5-methoxymethyloxy-1,3-dihydro-2H-benzimidazol-2-one One (1.00) g of 2-nitro-4-hydroxy-1-chlorobenzene was dissolved in 30 ml of chloroform, and to which 0.50 ml of chloromethyl methyl ether and 1.30 ml of diisopropylethylamine were added, followed by 30 minute' stirring at 0° C. The reaction liquid was diluted with ethyl acetate, washed with water and saturated brine, and dried over anhydrous sodium sulfate. The solvent was concentrated and the residue was reacted following Referential Example 5 to provide the title compound.

Referential Example 16

Preparation of 1-[1-(1-ethoxycarbonylpiperidin-4-yl)-piperidin-4-yl]-1,3-dihydro-2H-benzimidazol-2-one Forty-one (41) mg of 1-[1-(piperidin-4-yl)piperidin-4-yl]-1,3-dihydro-2H-benzimidazol-2-one.di-trifluoroacetate was dissolved in 5 ml of dichloromethane, and to which 25 mg of diisopropylethylamine and 11 mg of ethyl chloroformate were added, followed by stirring overnight. The reaction mixture was distributed between chloroform and saturated aqueous sodium bicarbonate solution. The organic layer was dried over sodium sulfate, concentrated, and the resulting residue was purified by silica gel column chromatography (chloroform/methanol=10/1). Thus 22 mg of the title compound was obtained as a colorless, amorphous substance.

Industrial Applicability

The compounds of the present invention are useful as analgesic for diseases accompanying pain such as cancerous pain, postoperative pain, migraine, gout, chronic rheumatism, chronic pain or neuralgia; or as agents for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflex esophagitis.

What is claimed is:

1. Compounds represented by a formula (I)

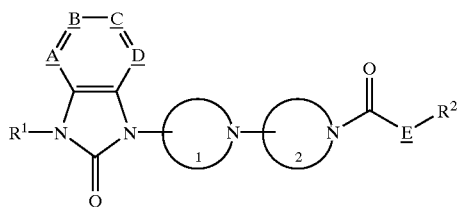

(I)

in which $\underline{A}$, $\underline{B}$, $\underline{C}$ and $\underline{D}$ are the same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy-carbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl)(lower alkyl)amino and (di-lower alkylaminosulfonyl)(lower alkyl)amino; $\underline{E}$ signifies oxygen or sulfur;

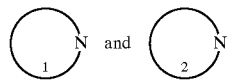

are the same or different and signify $C_3$–$C_9$ mono- or bi-cyclic aliphatic nitrogen-containing heterocyclic group(s) which may be substituted with halogen or lower alkyl; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino; and $R^2$ signifies lower alkyl; or salts thereof.

2. The compounds of claim 1, in which $\underline{A}$, $\underline{B}$, $\underline{C}$ and $\underline{D}$ are the same or different and signify methine group(s) which may be substituted with halogen, hydroxyl, lower alkylsulfonyl, optionally fluorine-substituted lower alkoxy, di(lower alkyl)carbamoyl or di(lower alkyl)aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, lower alkylcarbamoyloxy, di(lower alkyl)carbamoyloxy, lower alkoxy carbonylamino, aminosulfonyl, lower alkylaminosulfonyl, di(lower alkyl)aminosulfonyl, (lower alkylamino)sulfonylamino and (di-lower alkylamino)sulfonylamino.

3. The compounds of claim 1, in which $\underline{A}$, $\underline{B}$, $\underline{C}$ and $\underline{D}$ are the same or different and signify methine group(s) which may be substituted with halogen, hydroxyl or lower alkylsulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, lower alkylcarbamoyloxy, di(lower alkyl)carbamoyloxy, lower alkoxycarbonylamino, aminosulfonyl, lower alkylaminosulfonyl, di(lower alkyl)aminosulfonyl, (lower alkylamino)sulfonylamino and (di-lower alkylamino)sulfonylamino.

4. The compounds of claim 1, in which the $C_3$–$C_9$ mono- or bi-cyclic aliphatic nitrogen-containing heterocyclic groups of

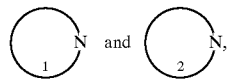

which are same or different, signify azetidine-1,3-di-yl, piperidine-1,4-di-yl, hexahydroazepine-1,4-di-yl, 3-azabicyclo[3.3.0]octane-3,7-di-yl or 8-azabicyclo[3.2.1]octane-3,8-di-yl groups.

5. The compounds of claim 1 in which both of

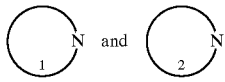

are piperidine-1,4-di-yl groups.

6. The compounds of claim 1, in which R¹ signifies lower alkenyl, cyclo(lower alkyl), lower alkoxycarbonyl or carbamoyl; lower alkylsulfonyl which may be substituted with halogen, hydroxyl or oxo; or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamnino, (lower alkylcarbamoyl)amino, (di-lower alkylcarbamoyl)amino, (lower alkylamino)sulfonylamino and (di-lower alkylamino)sulfonylamino.

7. The compounds of claim 1 in which R¹ signifies lower alkylsulfonyl whichmay be substituted with halogen, hydroxyl or oxo.

8. The compounds of claim 1 in which A̲, B̲, C̲ and D̲ are the same or different and signify methine group(s) which may be substituted with halogen, hydroxyl or lower alkylsulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, lower alkylcarbamoyloxy, di(lower alkyl)carbamoyloxy, lower alkoxycarbonylamino, aminosulfonyl, lower alkylaminosulfonyl, di(lower alkyl)aminosulfonyl, (lower alkylamino)sulfonylamino and (di-lower alkylamino)sulfonylamino; both

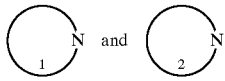

signify 1,4-piperidine-di-yl; and R¹ signifies a lower alkenyl, cyclo(lower alkyl), lower alkoxycarbonyl or carbamoyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino.

9. The compounds of claim 8, in which R¹ signifies lower alkylsulfonyl which may be substituted with halogen, hydroxyl or oxo.

10. The compounds of claim 1 which are:
1-[1-(1-methoxycarbonylpiperidin-4-yl)piperidin-4-yl]-3-(2-propynyl)-1,3-dihydro-2H-benzimidazol-2-one,
1-[1-(1-methoxycarbonylpiperidin-4-yl)piperidin-4-yl]-3-(2-propenyl)-1,3-dihydro-2H-benzimidazol-2-one,
1-[1-(1-methoxycarbonylpiperidin-4-yl)piperidin-4-yl]-3-n-butyl-1,3-dihydro-2H-benzimidazol-2-one,
1-[1-(1-methoxycarbonylpiperidin-4-yl)piperidin-4-yl]-3-methyl-1,3-dihydro-2H-benzimidazol-2-one,
1-[1-(1-methoxycarbonylpiperidin-4-yl)piperidin-4-yl]-3-(2,2,2-trifluoroethyl)-1,3-dihydro-2H-benzimidazol-2-one,
1-[1-(1-methoxycarbonylpiperidin-4-yl)piperidin-4-yl]-3-(methoxycarbonylmethyl)-1,3-dihydro-2H-benzimidazol-2-one,
1-[1-(1-methoxycarbonylpiperidin-4-yl)piperidin-4-yl]-3-(2-oxopropyl)-1,3-dihydro-2H-benzimidazol-2-one,
1-[1-(1-methoxycarbonylpiperidin-4-yl)piperidin-4-yl]-3-(2-aminoethyl)-1,3-dihydro-2H-benzimidazol-2-one,
1-[1-(1-methoxycarbonylpiperidin-4-yl)piperidin-4-yl]-3-(dimethylaminosulfonyl)-1,3-dihydro-2H-benzimidazol-2-one,
1-[1-(1-methoxycarbonylpiperidin-4-yl)piperidin-4-yl]-3-ethyl-1,3-dihydro-2H-benzimidazol-2-one,
1-[1-(1-methoxycarbonylpiperidin-4-yl)piperidin-4-yl]-3-n-propyl-1,3-dihydro-2H-benzimidazol-2-one,
1-[1-(1-methoxycarbonylpiperidin-4-yl)piperidin-4-yl]-3-acetyl-1,3-dihydro-2H-benzimidazol-2-one,
1-[1-(1-methoxycarbonylpiperidin-4-yl)piperidin-4-yl]-3-(methylsulfonyl)-1,3-dihydro-2H-benzimidazol-2-one,
1-[1-(1-methoxycarbonylpiperidin-4-yl)piperidin-4-yl]-3-(methoxycarbonyl)-1,3-dihydro-2H-benzimidazol-2-one,
1-[1-(1-methoxycarbonylazetidin-3-yl)piperidin-4-yl]-3-(methyl-sulfonyl)-1,3-dihydro-2H-benzimidazol-2-one,
1-[1-(1-methoxycarbonylpiperidin-4-yl)azetidin-3-yl]-3-(methyl-sulfonyl)-1,3-dihydro-2H-benzimidazol-2-one,
1-[1-(1-methoxycarbonylpiperidin-4-yl)piperidin-4-yl]-5-methyl-3-(methylsulfonyl)-1,3-dihydro-2H-benzimidazol-2-one,
1-[1-(1-methoxycarbonylpiperidin-4-yl)piperidin-4-yl]4-fluoro-3-(methylsulfonyl)-1,3-dihydro-2H-benzimidazol-2-one,
1-[1-(1-methoxycarbonylpiperidin-4-yl)piperidin-4-yl]-3-(methylsulfonyl)-1,3-dihydro-2H-imidazo[4,5-b]pyridin-2-one,
1-[1-(1-ethoxycarbonylpiperidin-4-yl)piperidin-4-yl]-3-(methylsulfonyl)-1,3-dihydro-2H-benzimidazol-2-one,
1-[1-(1-methoxycarbonylpiperidin-4-yl)piperidin-4-yl]-3-(2-fluoroethyl)-1,3-dihydro-2H-benzimidazol-2-one,
1-[1-(1-methoxycarbonylpiperidin-4-yl)piperidin-4-yl]-3-(2,2-difluoroethyl)-1,3-dihydro-2H-benzimidazol-2-one,
1-[1-(1-methoxycarbonylpiperidin-4-yl)piperidin-4-yl]-3-(3,3,3-trifluoropropyl)-1,3-dihydro-2H-benzimidazol-2-one,
1-[1-(1-methoxycarbonylpiperidin-4-yl)piperidin-4-yl]-3-(2-hydroxyethyl)-1,3-dihydro-2H-benzimidazol-2-one,
1-[1-(1-methoxycarbonylpiperidin-4-yl)piperidin-4-yl]-3-prenyl-1,3-dihydro-2H-benzimidazol-2-one,
1-[1-(1-methoxycarbonylpiperidin-4-yl)piperidin-4-yl]-3-(ethylsulfonyl)-1,3-dihydro-2H-benzimidazol-2-one,
1-[1-(1-methoxycarbonylpiperidin-4-yl)piperidin-4-yl]-3-(isopropylsulfonyl)-1,3-dihydro-2H-benzimidazol-2-one,
1-[1-(1-methoxycarbonylpiperidin-4-yl)piperidin-4-yl]-3-(n-butylsulfonyl)-1,3-dihydro-2H-benzimidazol-2-one,
1-[1-(1-methoxycarbonylpiperidin-4-yl)piperidin-4-yl]-3-carbomyl-1,3-dihydro-2H-benzimidazol-2-one,
1-[1-(1-methoxycarbonylpiperidin-4-yl)piperidin-4-yl]-3-(ethoxycarbonylmethyl)-1,3-dihydro-2H-benzimidazol-2-one, 1-[1-(1-methoxycarbonylpiperidin-4-yl)piperidin-4-yl]-3-(2-oxo-n-butyl)-1,3-dihydro-2H-benzimidazol-2-one,
1-[1-(1-methoxycarbonylpiperidin-4-yl)piperidin-4-y]-3-(methylsulfonylmethyl)-1,3-dihydro-2H-benzimidazol-2-one,
1-[1-(1-methoxycarbonylpiperidin-4-yl)piperidin-4-yl]-3-(methylthiomethyl)-1,3-dihydro-2H-benzimidazol-2-one,
1-[1-(1-methoxycarbonylpiperdin-4-yl)piperidin-4-yl]-3-(2-methylsulfonylethyl)-1,3-dihydro-2H-benzimidazol-2-one,
1-[1-(1-methoxycarbonylpiperidin-4-yl)piperidin-4-yl]-3-(2-methylthioethyl)-1,3-dihydro-2H-benzimidazol-2-one,
1-[1-(1-methoxycarbonylpiperidin-4-yl)piperidin-4-yl]-3-(2-ethoxyethyl)-1,3-dihydro-2H-benzimidazol-2-one,
1-[1-(1-ethoxycarbonylpiperidin-4-yl)piperidin-4-yl]-3-methyl-1,3-dihydro-2H-benzimidazol-2-one,
1-[1-(1-methoxycarbonylpiperidin-4-yl)piperidin-4-yl]-3-methyl-4-(methylsulfonyl)-1,3-dihydro-2H-benzimidazol-2-one,
1-[1-(1-methoxycarbonylpiperidin-4-yl)piperidin-4-yl]-3-methyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(ethylsulfonylmethyl)-1,3-dihydro-2H-benzimidazol-2-one,
1-[1-(1-methoxycarbonylpiperidin-4-yl)piperidin-4-yl]-3-methyl-4-(methoxycarbonylamino)methyl-1,3-dihydro-2H-benzimidazol-2-one
1-[1-(1-methoxycarbonylpiperidin-4-yl)piperidin-4-yl]-3-ethyl-4-(methoxycarbonylamino)methyl-1,3-dihydro-2H-benzimidazol-2-one,
1-[1-(1-methoxycarbonylpiperidin-4-yl)piperidin-4-yl]-3-(methylsulfonyl)-4-hydroxy-1,3-dihydro-2H-benzimidazol-2-one,
1-[1-(1-methoxycarbonylpiperidin-4-yl)piperidin-4-yl]-3-(methylsulfonyl)-5-hydroxy-1,3-dihydro-2H-benzimidazol-2-one,
1-[1-(1-methoxycarbonylpiperidin-4-yl)piperidin-4-yl]-3-(methylsulfonyl)-6-hydroxy-1,3-dihydro-2H-benzimidazol-2-one,
1-[1-(1-methoxycarbonylpiperidin-4-yl)piperidin-4-yl]-3-(methylsulfonyl)-5-bromo-1,3-dihydro-2H-benzimidazol-2-one,
1-[1-(1-methoxycarbonylpiperidin-4-yl)piperidin-4-yl]-3-(methylsulfonyl)-5-fluoro-1,3-dihydro-2H-benzimidazol-2-one,
1-[1-(1-methoxycarbonylpiperidin-4-yl)piperidin-4-yl]-3-(methylsulfonyl)-6-fluoro-1,3-dihydro-2H-benzimidazol-2-one, and
1-[1-(1-ethoxycarbonylpiperidin-4-yl)piperidin-4-yl]-3-(ethoxycarbonyl)-1,3-dihydro-2H-benzimidazol-2-one.

11. The compounds of claim 1 which are:
1-[1-(1-methoxycarbonylpiperidin-4-yl)piperidin-4-yl]-3-methyl-1,3-dihydro-2H-benzimidazol-2-one,
1-[1-(1-methoxycarbonylpiperidin-4-yl)piperidin-4-yl]-3-(methoxycarbonylmethyl)-1,3-dihydro-2H-benzimidazol-2-one,
1-[1-(1-methoxycarbonylpiperidin-4-yl)piperidin-4-yl]-3-ethyl-1,3-dihydro-2H-benzimidazol-2-one,
1-[1-(1-methoxycarbonylpiperidin-4-yl)piperidin-4-yl]-3-n-propyl-1,3-dihydro-2H-benzimidazol-2-one,
1-[1-(1-methoxycarbonylpiperidin-4-yl)piperidin-4-yl]-3-(2-hydroxyethyl)-1,3-dihydro-2H-benzimidazol-2-one,
1-[1-(1-methoxycarbonylpiperidin-4-yl)piperidin-4-yl]-3-(2-aminoethyl)-1,3-dihydro-2H-benzimidazol-2-one,
1-[1-(1-methoxycarbonylpiperidin-4-yl)piperidin-4-yl]-3-(methoxycarbonyl)-1,3-dihydro-2H-benzimidazol-2-one,
1-[1-(1-methoxycarbonylpiperidin-4-yl)piperidin-4-yl]-3-(methylsulfonyl)-1,3-dihydro-2H-benzimidazol-2-one,
1-[1-(1-methoxycarbonylpiperidin-4-yl)piperidin-4-yl]-3-(ethylsulfonyl)-1,3-dihydro-2H-benzimidazol-2-one,
1-[1-(1-methoxycarbonylpiperidin-4-yl)piperidin-4-yl]-5-methyl-3-(methylsulfonyl)-1,3-dihydro-2H-benzimidazol-2-one,
1-[1-(1-methoxycarbonylpiperidin-4-yl)piperidin-4-yl]-4-fluoro-3-(methylsulfonyl)-1,3-dihydro-2H-benzimidazol-2-one,
1-[1-(1-methoxycarbonylpiperidin-4-yl)piperidin-4-yl]-3-(methylsulfonyl)-5-fluoro-1,3-dihydro-2H-benzimidazol-2-one,
1-[1-(1-methoxycarbonylpiperidin-4-yl)piperidin-4-yl]-3-(methylsulfonyl)-6-fluoro-1,3-dihydro-2H-benzimidazol-2-one,
1-[1-(1-methoxycarbonylpiperidin-4-yl)piperidin-4-yl]-3-(2-fluoroethyl)-1,3-dihydro-2H-benzimidazol-2-one,
1-[1-(1-methoxycarbonylpiperidin-4-yl)piperidin-4-yl]-3-(2,2-difluoroethyl)-1,3-dihydro-2H-benzimidazol-2-one,
1-[1-(1-methoxycarbonylpiperidin-4-yl)piperidin-4-yl]-3-methyl-4-(methylsulfonyl)-1,3-dihydro-2H-benzimidazol-2-one,
1-[1-(1-methoxycarbonylpiperidin-4-yl)piperidin-4-yl]-3-methyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(methylsulfonylmethyl)-1,3-dihydro-2H-benzimidazol-2-one,
1-[1-(1-methoxycarbonylpiperidin-4-yl)piperidin-4-yl]-3-ethyl-4-(ethylsulfonylmethyl)-1,3-dihydro-2H-benzimidazol-2-one,
1-[1-(1-methoxycarbonylpiperidin-4-yl)piperidin-4-yl]-3-methyl-4-(methoxycarbonylamino)methyl-1,3-dihydro-2H-benzimidazol-2-one and
1-[1-(1-methoxycarbonylpiperidin-4-yl)piperidin-4-yl]-3-ethyl-4-(methoxycarbonylamino)methyl-1,3-dihydro-2H-benzimidazol-2-one.

12. A method for producing a compound represented by the formula (I)

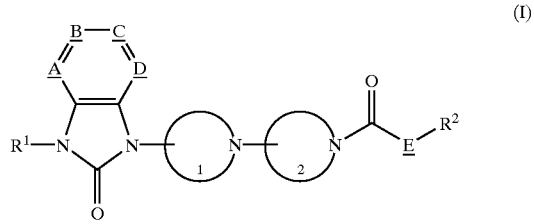

(I)

in which A, B, C and D are the same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl) aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl)(lower alkyl)amino and (di-lower alkylaminosulfonyl)(lower alkyl)amino; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino; $\underline{E}$,

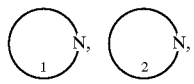

and $R^2$ have the later defined significance or a salt thereof, which comprises reacting a compound represented by formula (VII)

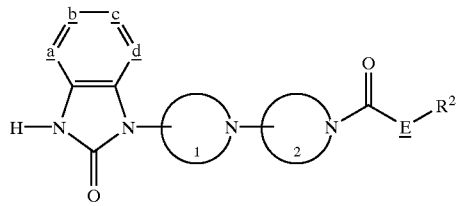

(VII)

in which $\underline{a}$, $\underline{b}$, $\underline{c}$ and $\underline{d}$ are the same or different and signify methine group(s) or nitrogen atom, said methine group(s) being optionally substituted with cyano, halogen, optionally protected hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, lower alkoxycarbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl)(lower alkyl)amino, (di-lower alkylaminosulfonyl)(lower alkyl)amino, and optionally protected hydroxyl, amino and lower alkylamino; $\underline{E}$ signifies oxygen or sulfur;

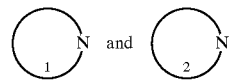

are same or different and signify $C_3$–$C_9$ mono- or bi-cyclic aliphatic nitrogen-containing heterocyclic group(s) which may be substituted with halogen or lower alkyl; and $R^2$ is lower alkyl with a compound represented by a general formula (VIII)

$$R^{1p}—L^2 \quad (VIII)$$

in which $L^2$ signifies a leaving group, and $R^{1p}$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, optionally protected hydroxyl or oxo, or lower alkyl which may have a substituent selected from the group consisting of cyano, halogen, oxo, cyclo(lower alkyl), optionally fluorine-substituted lower alkoxy, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino, and optionally protected hydroxyl, amino and lower alkylamino to form a compound represented by formula (IV)

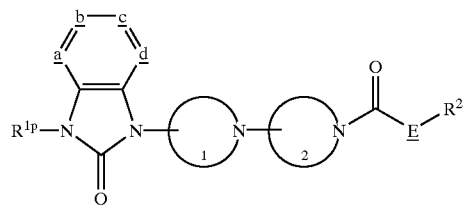

(IV)

in which $\underline{a}$, $\underline{b}$, $\underline{c}$, $\underline{d}$, $\underline{E}$,

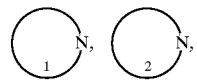

$R^{1p}$ and $R^2$ have the earlier given significance; and if necessary removing protective group(s).

13. A method for producing a compound represented by the formula (I)

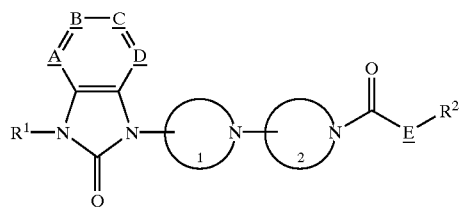

(I)

in which $\underline{A}$, $\underline{B}$, $\underline{C}$ and $\underline{D}$ are same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl) aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl) aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino; $\underline{E}$,

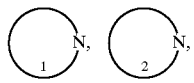

and $R^2$ have the later defined significance;

or a salt thereof, which comprises reacting a compound represented by formula (IX)

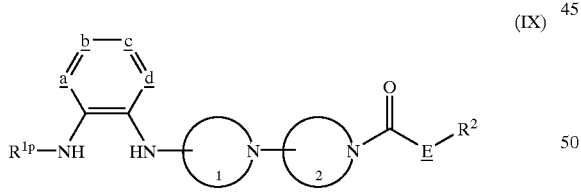

(IX)

in which $\underline{a}$, $\underline{b}$, $\underline{c}$ and $\underline{d}$ are same or differtent and signify methine group(s) or nitrogen atom, said methine group (s) being optionally substituted with cyano, halogen, optionally protected hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl) carbamoyl, aminosulfonyl, lower alkylaminosulfonyl or di(lower alkyl)aminosulfonyl, or lower alkyl which may have a substituent selected from the group consisting of halogen, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxycarbonylamino, aminosulfonyl, lower alkylaminosulfonyl, di(lower alkyl)aminosulfonyl, (lower alkylamino) sulfonylamino, (di-lower alkylamino)sulfonylamino, (lower alkylaminosulfonyl)(lower alkyl)amino, (di-lower alkylaminosulfonyl)(lower alkyl)amino, and optionally protected hydroxyl, amino and lower alkylamino; $\underline{E}$ signifies oxygen or sulfur;

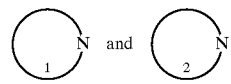

are same or different and signify $C_3$–$C_9$ mono- or bi-cyclic aliphatic nitrogen-containing heterocyclic group(s) which may be substituted with halogen or lower alkyl; $R^{1p}$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, optionally protected hydroxyl or oxo, or lower alkyl which may have a substituent selected from the group consisting of cyano, halogen, oxo, cyclo(lower alkyl), optionally fluorine-substituted lower alkoxy, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl) amino, (lower alkylamino)sulfonylamino and (di-lower alkylamino)sulfonylamino, and optionally protected hydroxyl, amino and lower alkylamino; and $R^2$ signifies lower alkyl; with a compound selected from the group consisting of carbonyldiimidazole, triphosgene, diphosgene, methyl chloroformate, ethyl chloroformate, dimethyl carbonate and diethyl carbonate, to form a compound represented by the formula (IV),

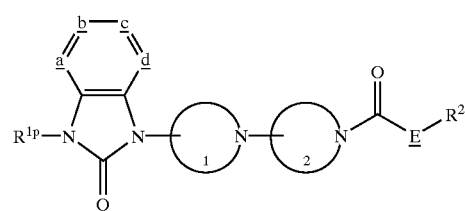

(IV)

in which $\underline{a}$, $\underline{b}$, $\underline{c}$, $\underline{d}$, $\underline{E}$,

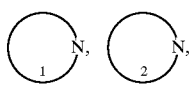

$R^{1p}$ and $R^2$ have the earlier given significance; and if necessary removing protective group(s).

14. A pharmaceutical composition comprising therapeutically effective amount of a compound represented by the formula (I)

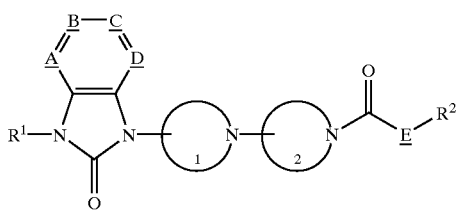

in which A, B, C and D are same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl)(lower alkyl)amino and (di-lower alkylaminosulfonyl)(lower alkyl)amino; E signifies oxygen or sulfur;

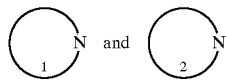

are same or different and signify $C_3$–$C_9$ mono- or bi-cyclic aliphatic nitrogen-containing heterocyclic group(s) which may be substituted with halogen or lower alkyl; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl)amino, (lower alkylamino)sulfonylamino and (di-lower alkylamino)sulfonylamino; and $R^2$ signifies lower alkyl;

or a salt thereof and at least one pharmaceutically acceptable adjuvant.

15. A composition comprising a muscarinic M4 receptor agonistic effective amount of a compound represented by the formula (I)

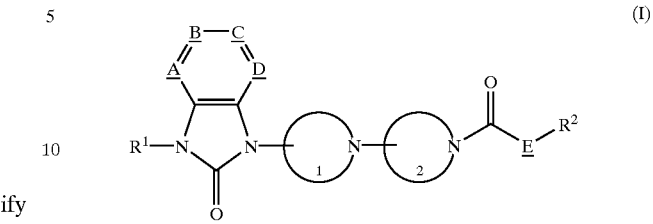

in which A, B, C and D are same or different and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl)aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino; E signifies oxygen or sulfur;

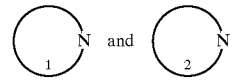

are same or different and signify $C_3$–$C_9$ mono- or bi-cyclic aliphatic nitrogen-containing heterocyclic group(s) which may be substituted with halogen or lower alkyl; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl) carbamoyloxy, aminosulfonyl, lower alkylaminosulfonyl, di(lower alkyl)aminosulfonyl, lower alkylsulfonylamino, (lower alkylcarbamoyl)amino, (di-lower alkylcarbamoyl) amino, (lower alkylamino)sulfonylamino and (di-lower alkylamino)sulfonylamino; and $R^2$ signifies lower alkyl;

or a salt thereof and an inert carrier.

16. A method for treating tolerance to narcotic analgesics represented by morphine, dependence on narcotic analgesics represented by morphine, itching, dementia, irritable bowel syndrome, schizophrenia, glaucoma, pollakiuria, urinary incontinence, cholelithiasis, cholecystitis, functional dyspepsia and reflux esophagitis, which comprises administering a therapeutically effective amount of a compound of the formula (I)

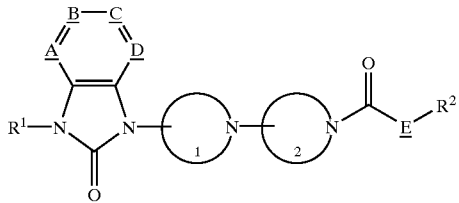

in which A, B, C and D are same or differtent and signify methine group(s) or nitrogen atom, said methine group(s) being optionally substituted with cyano, halogen, hydroxyl, cyclo(lower alkyl), lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, aminosulfonyl, lower alkylaminosulfonyl or di(lower alkyl) aminosulfonyl, or lower alkyl which may have a substituent selected from the group consisting of halogen, hydroxyl, amino, lower alkylamino, di(lower alkyl)amino, lower alkylthio, lower alkylsulfinyl, lower alkylsulfonyl, optionally fluorine-substituted lower alkoxy, lower alkanoyl, lower alkoxycarbonyl, carbamoyl, lower alkylcarbamoyl, di(lower alkyl)carbamoyl, carbamoyloxy, lower alkylcarbamoyloxy, di(lower alkyl)carbamoyloxy, lower alkoxy carbonylamino, aminosulfonyl, lower alkylaminosulfonyl, di(lower alkyl) aminosulfonyl, (lower alkylamino)sulfonylamino, (di-lower alkylamino)sulfonylamino, (lower alkylaminosulfonyl) (lower alkyl)amino and (di-lower alkylaminosulfonyl) (lower alkyl)amino; E signifies oxygen or sulfur;

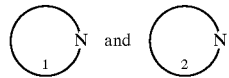

are same or different and signify $C_3$–$C_9$ mono- or bi-cyclic aliphatic nitrogen-containing heterocyclic group(s) which may be substituted with halogen or lower alkyl; $R^1$ signifies lower alkenyl, lower alkynyl, cyclo(lower alkyl), lower alkanoyl, lower alkoxycarbonyl, carbamoyl, lower alkylcarbamoyl, di(lower alkyl)carbamoyl, aminosulfonyl, lower alkylaminosulfonyl or di(lower alkyl)aminosulfonyl, or lower alkylsulfonyl which may be substituted with halogen, hydroxyl or oxo, or lower alkyl which may have a substituent selected from the group consisting of cyano, halogen, hydroxyl, oxo, amino, cyclo(lower alkyl), optionally fluorine-substituted lower alkoxy, lower alkylamino, di(lower alkyl)amino, lower alkylthio, lower alkylsulfinyl, lower alkylsulfonyl, lower alkoxycarbonyl, carbamoyl, lower alkylcarbamoyl, di(lower alkyl)carbamoyl, carbamoyloxy, lower alkylcarbamoyloxy, di(lower alkyl) carbamoyloxy, aminosulfonyl, lower alkylamino-sulfonyl, di(lower alkyl)aminosulfonyl, lower alkylsulfonylamino, (lower alkylcarbamoyl)amino, (di-lower alkylcarbamoyl) amino, (lower alkylamino)sulfonylamino and (di-lower alkylamino)sulfonylamino; and $R^2$ signifies lower alkyl; or a salt thereof.

* * * * *